United States Patent [19]
Koutrakis et al.

[11] Patent Number: 5,932,795
[45] Date of Patent: Aug. 3, 1999

[54] METHODS AND APPARATUS FOR CONTINUOUS AMBIENT PARTICULATE MASS MONITORING

[75] Inventors: Petros Koutrakis, Wellesley; Peng-Yau Wang, Cambridge; Jack Mikhail Wolfson, Jamaica Plain; Constantinos Sioutas, Boston, all of Mass.

[73] Assignee: President and Fellows of Harvard College, Boston, Mass.

[21] Appl. No.: 08/785,929

[22] Filed: Jan. 22, 1997

[51] Int. Cl.[6] .............................. G01N 15/02; B07B 7/86; G01T 1/16
[52] U.S. Cl. .................... 73/28.01; 73/28.05; 73/863.22; 73/865.5; 422/80
[58] Field of Search ................................ 73/28.01, 28.05, 73/865.5; 422/80

[56] References Cited

U.S. PATENT DOCUMENTS

| | | | |
|---|---|---|---|
| 4,056,969 | 11/1977 | Barringer | 73/28 |
| 4,117,715 | 10/1978 | Hoening | 73/28 |
| 4,132,894 | 1/1979 | Yule | 250/435 |
| 4,246,788 | 1/1981 | Olin et al. | 73/421.5 R |
| 4,301,002 | 11/1981 | Loo et al. | 209/143 |
| 4,550,591 | 11/1985 | Cox et al. | 73/28 |
| 4,670,135 | 6/1987 | Marple et al. | 509/143 |
| 4,685,066 | 8/1987 | Hafele et al. | 364/509 |
| 5,040,424 | 8/1991 | Marple et al. | 73/863.23 |
| 5,090,233 | 2/1992 | Kogure et al. | 73/28.05 |
| 5,239,861 | 8/1993 | Fujita et al. | 73/61.43 |
| 5,317,930 | 6/1994 | Wedding | 73/863.03 |
| 5,369,981 | 12/1994 | Merz et al. | 73/28.01 |
| 5,401,468 | 3/1995 | Patashnick et al. | 422/80 |
| 5,498,271 | 3/1996 | Marple et al. | 55/321 |

FOREIGN PATENT DOCUMENTS

| | | |
|---|---|---|
| 23 56 575 | 5/1975 | Germany . |
| 2 251 068 | 6/1992 | United Kingdom . |
| 92/21013 | 11/1992 | WIPO . |
| 96/28718 | 9/1996 | WIPO . |

OTHER PUBLICATIONS

Baron, "Calibration and Use of the Aerodynamic Particle Sizer (APS 3300)," *Aerosol Science and Technology* 5:55–67 (1986).

Chuan, "Rapid Measurement of Particulate Size Distribution in the Atmosphere," in *Fine Particles*, edited by B.Y.H. Liu, Academic Press Inc., New York, New York, pp. 763–775 (1976).

Daley and Lundgren, "The Performance of Piezoelectric Crystal Sensors Used to Determine Aerosol Mass Concentrations," *American Industrial Hygiene Association Journal* 36:518–532 (1975).

Hering et al., "Particle Measurements for the Children's Health Study: Development of a Two–Week Sampler," *6th Conference of the Intl. Soc. for Environ. Epid./4th Conference of the Intl. Soc. for Expos, Anal. (joint conference)*, Research Park Triangle, North Carolina, Sep. 1994, abstract No. 260.

Hinds, in *Aerosol Technology*, John Wiley & Sons Inc., New York, New York, pp. 44–47, 49–50 111–113 (1982).

John and Reischl, "Anomalous Filtration of Solid Particles by Nuclepore Filters," *Atmospheric Environment* 12:1555–1557 (1978).

(List continued on next page.)

*Primary Examiner*—Hezron E. Williams
*Assistant Examiner*—J. David Wiggins
*Attorney, Agent, or Firm*—Lyon & Lyon LLP

[57] ABSTRACT

Methods and apparatus for the continuous monitoring of ambient particulate mass in a gas sample encompassing the monitoring of $PM_{10}$, (particulate matter greater than 10 $\mu$m) and coarse particles (2.5 to 10 $\mu$m), the determination of the size distribution of particles, the determination of particle density and the determination of particle-bound water, utilizing such laboratory equipment as an inertial impactor, a virtual impactor, diffusion dryer(s), HEPA filter(s), particulate matter collector(s), and pressure transducer(s).

6 Claims, 6 Drawing Sheets

OTHER PUBLICATIONS

Koutrakis et al., "Development of a Continous Mass Monitor by Measuring Pressure Drop Across Filters," *Abstract for EPA/A&WMA Conference*, Research Triangle Park, NC, May 7–9 (1996) pp. 88–89.

Koutrakis et al., "Equilibrium Size of Atmospheric Aerosol Sulfates as a Function of Relative Humidity," *Journal of Geophysical Research* 94(D5):6442–6448 (1989).

Koutrakis et al., "Equilibrium Size of Atmospheric Aerosol Sulfates as a Function of the Particle Acidity and Ambient Relative Humidity," *Journal of Geophysical Research* 98(D4):7141–7147 (1993).

Lundgren et al., "Aerosol Mass Measurement Using Piezoelectric Crystal Sensors," in *Fine Particles*, edited by B.Y.H. Liu, Academic Press Inc., New York, New York, pp. 486–510 (1976).

Marple et al., "A Microorifice Uniform Deposit Impactor (Moudi): Description, Calibration, and Use," *Aerosol Science and Technology* 14:434–446 (1991).

Marple et al., "Low Flow Rate Sharp Cut Impactors for Indoor Air Sampling: Design and Calibration," *JAPCA* 37:1303–1307 (1987).

Marple and Chien, "Virtual Impactors: A Theoretical Study," *Environmental Science & Technology* 14(8):976–985 (1980).

McMurray and Stolzenburg, "On the Sensitivity of Particle Size to Relative Humidity for Los Angeles Aerosols," *Atmospheric Environment* 23(2):497–507 (1989).

Meyer et al., "Consideration for the Sampling and Measurement of Ambient Particulate Mass," *Proceedings of A&WMA Conference*, Pittsburg, PA, Apr. 4–6 (1995) pp. 204–210.

Patashnick and Rupprecht, "Continuous PM–10 Measurements Using the Tapered Element Oscillating Microbalance," *JAWMA* 41:1079–1083 (1991).

Pope et al., "Respiratory Health and $PM_{10}$ Pollution," *Am. Rev. Resp. Dis.* 144:668–674 (1991).

Rao and Whitby, "Non–Ideal Collection Characteristics of Inertial Impactors—II. Cascade Impactors," *Journal of Aerosol Science* 9:87–100 (1978).

Schwartz and Dockery, "Increased Mortality in Philadelphia Associated with Daily Air Pollution Concentrations[1–4]," *Am. Rev. Resp. Dis.* 145:600–604 (1992).

Sioutas et al., "Particle Loss in Glass Honeycomb Denuder Samplers," *Aerosol Science and Technology* 21:137–148 (1994).

Smith and Phillips, "Inertial Collection of Aerosol Particles at Circular Aperture," *Environ. Science & Technol.* 9:564–568 (1975).

Spurny et al., "Aerosol Filtration by Means of Nucleopore Filters: Structural and Filtration Properties," *Environ. Science & Technol.* 3:453–464 (1969).

Spurny et al., "Aerosol Filtration by Means of Nucleopore Filters: Aerosol Sampling and Measurement," *Environ, Science & Technol.* 3:464–468 (1969).

Tang et al., "Aerosol Growth Studies—IV. Phase Transformation of Mixed Salt Aerosols in a Moist Atmosphere," *Journal of Aerosol Science* 9:505–511 (1978).

Tang, "On the Equilibrium Partial Pressures of Nitric Acid and Ammonia in the Atmosphere," *Atmospheric Environment* 14:819–828 (1980).

Tang, "Phase Transformation and Growth of Aerosol Particles Composed of Mixed Salts," *Journal of Aerosol Science* 7:361–371 (1976).

Wilson and Liu, "Aerodynamic Particle Size Measurement by Laser–Doppler Velocimetry," *Journal of Aerosol Science* 11:139–150 (1980).

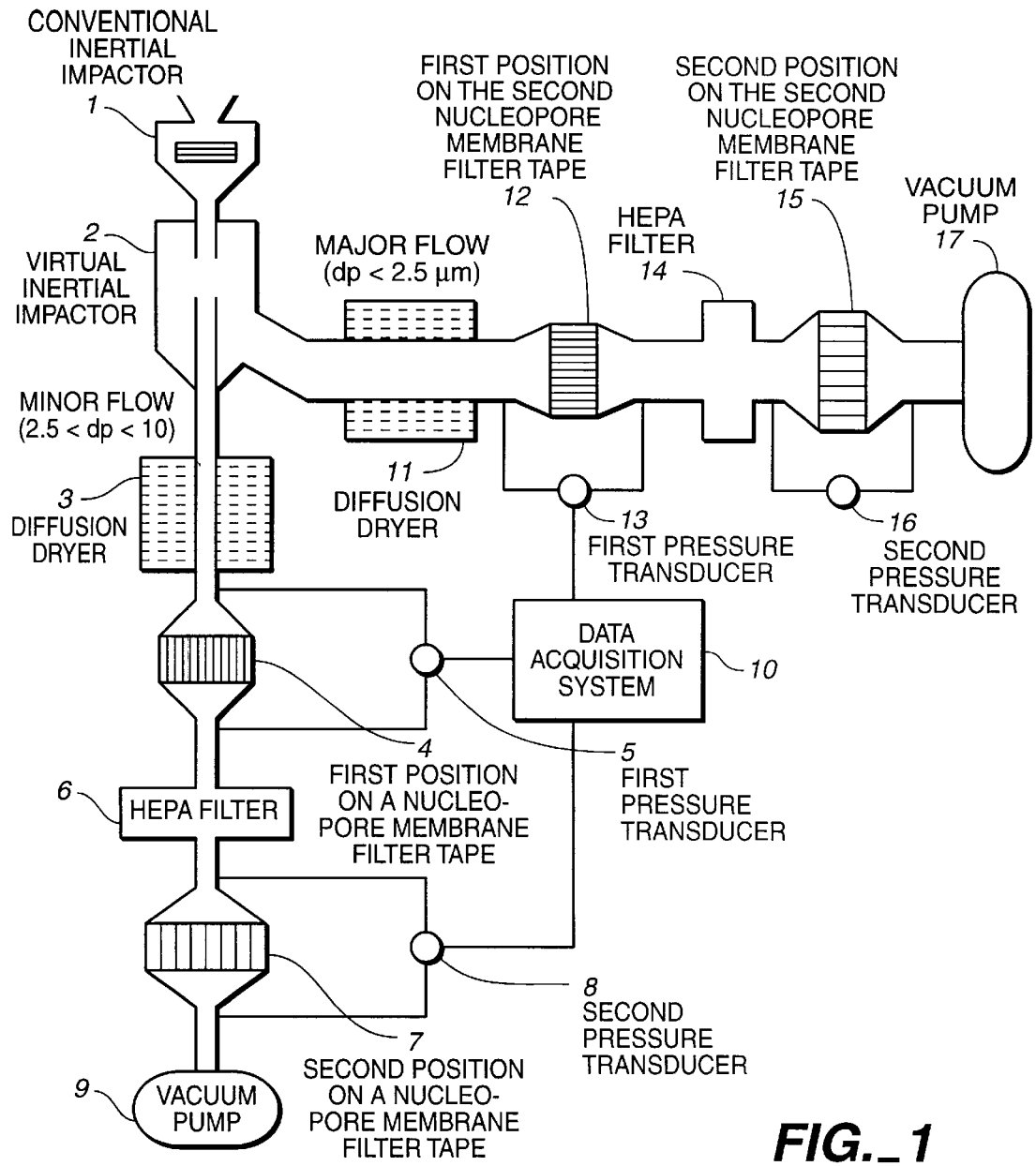
FIG._1

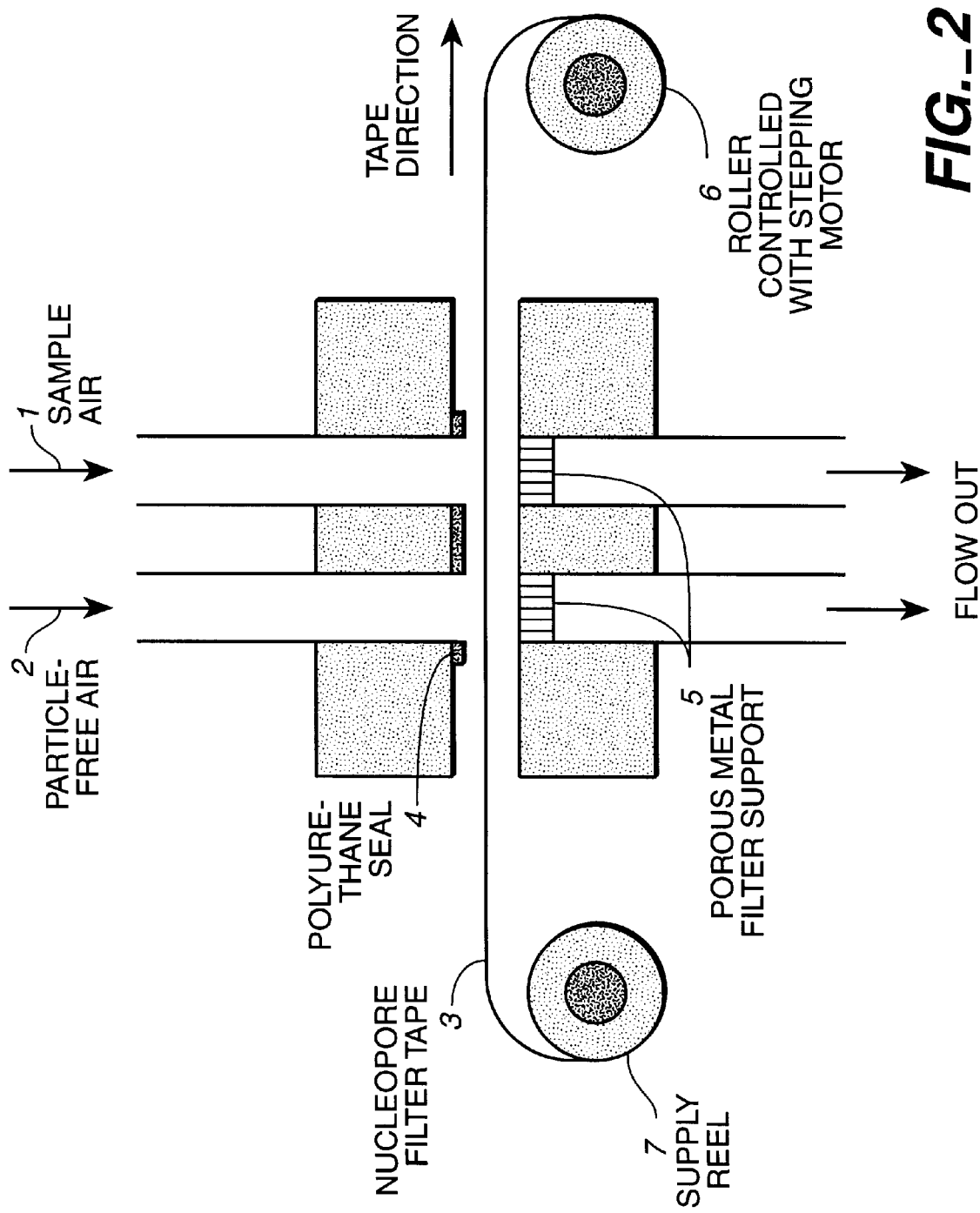
FIG._2

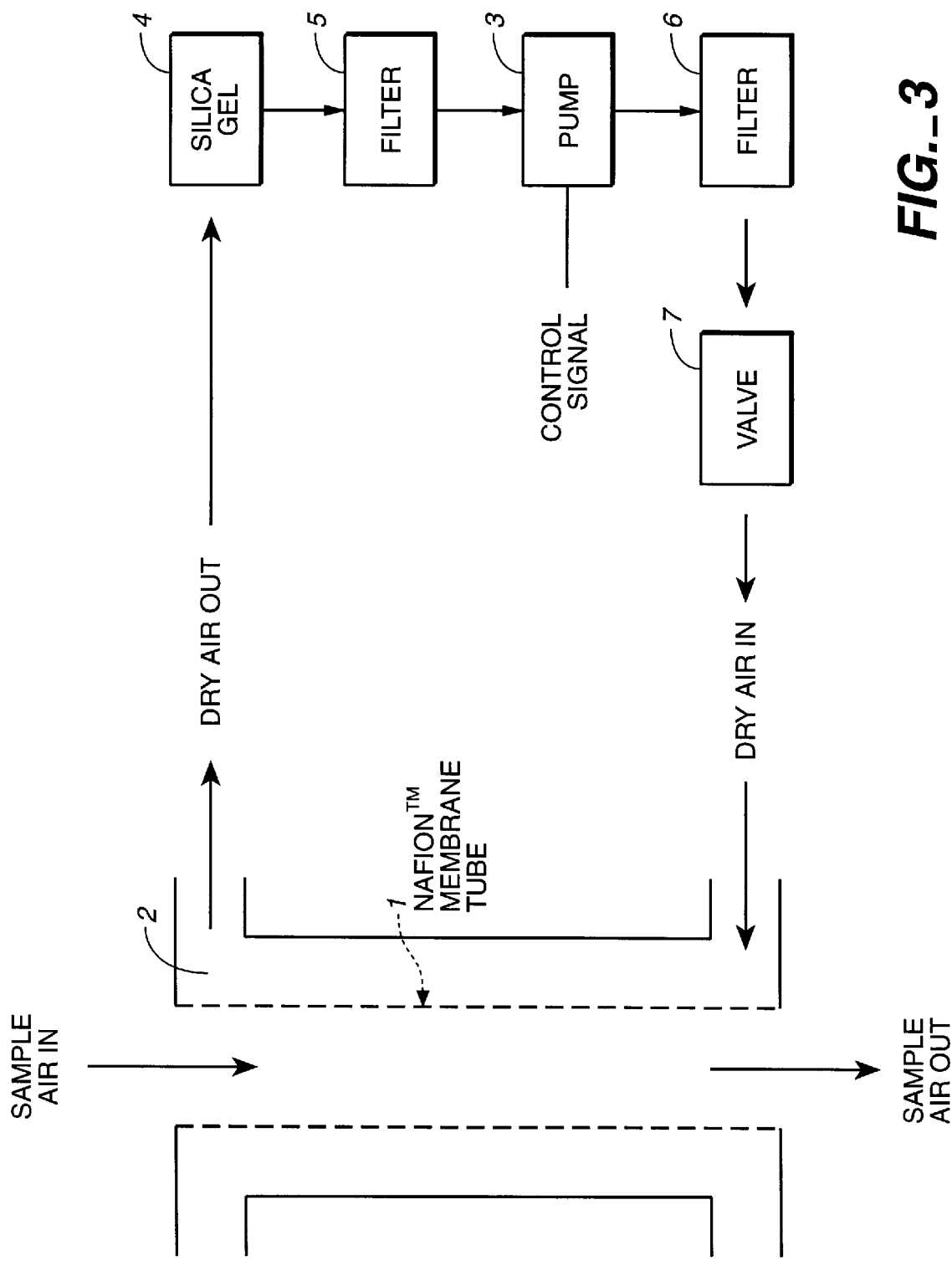
FIG._3

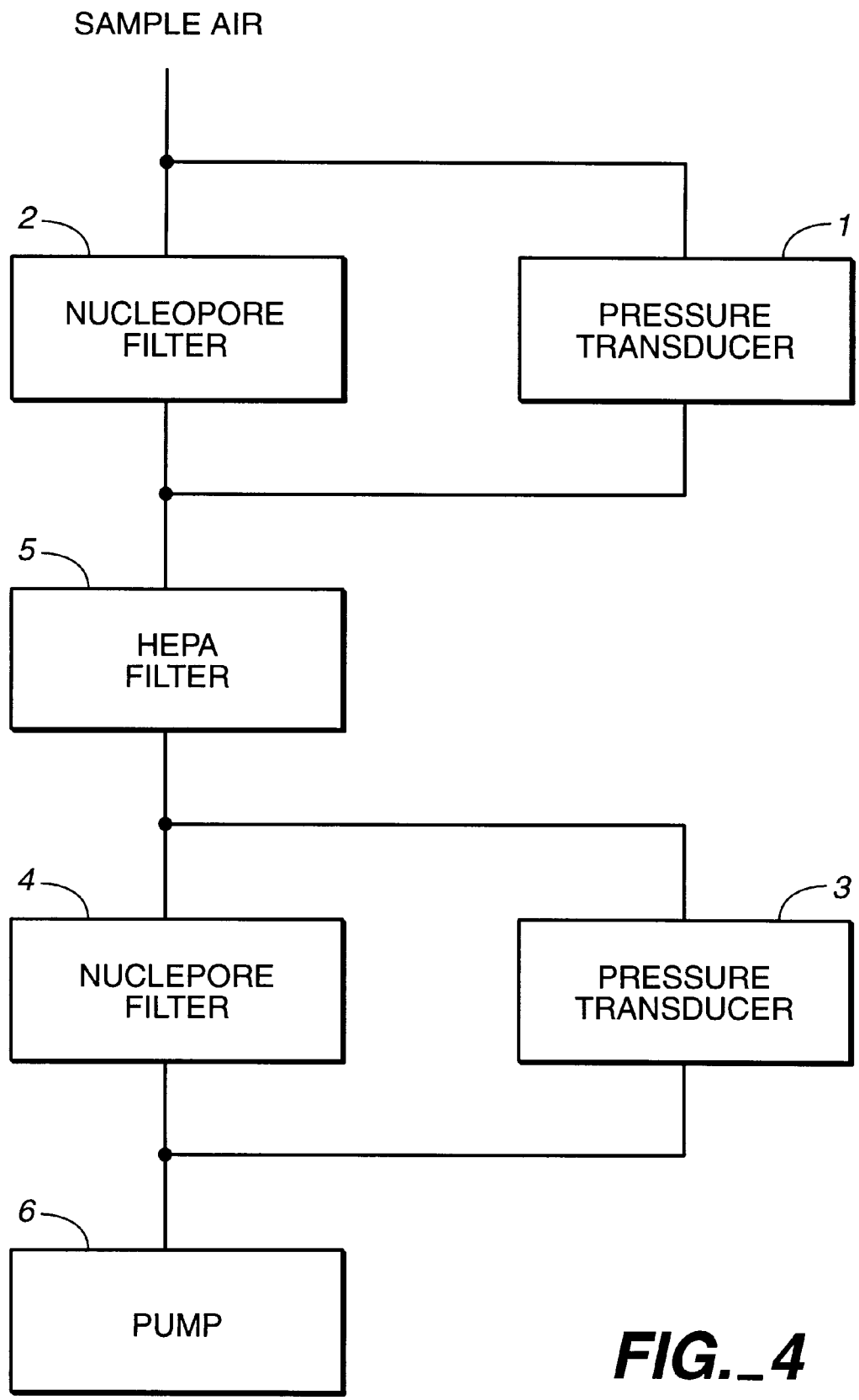
FIG._4

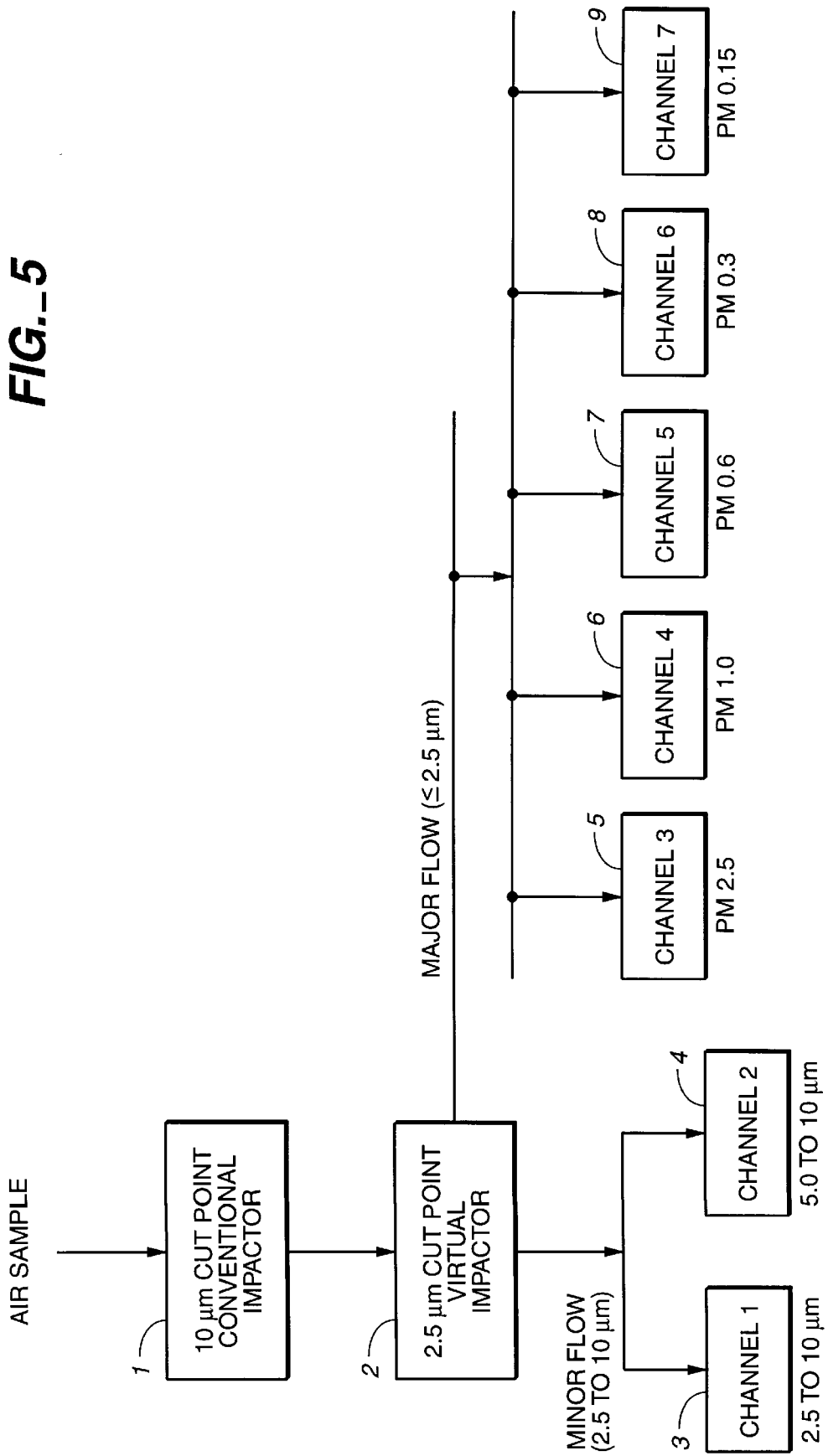
FIG._5

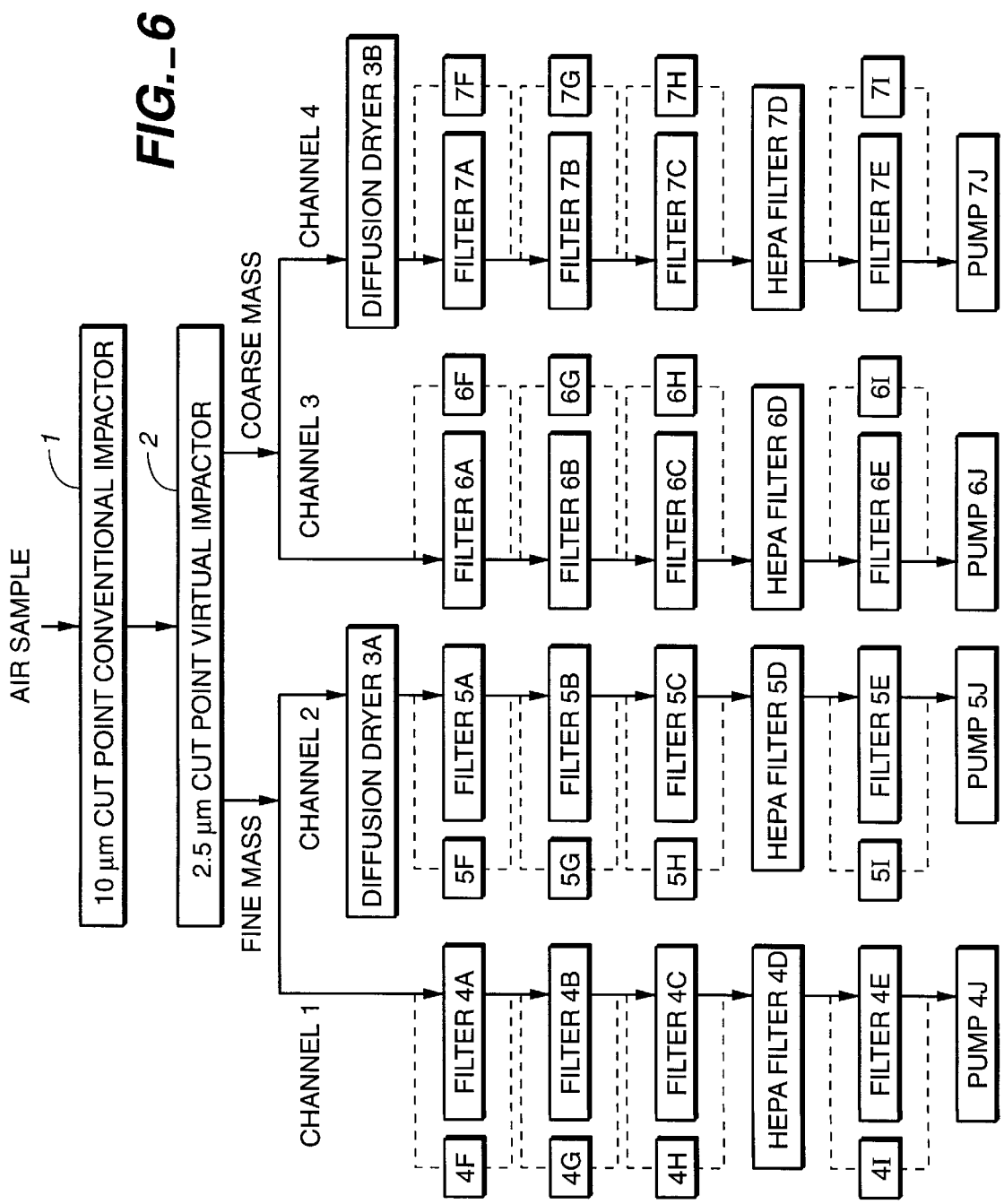

METHODS AND APPARATUS FOR CONTINUOUS AMBIENT PARTICULATE MASS MONITORING

FIELD OF THE INVENTION

This invention relates to methods for measuring particulate matter in gas, such as for environmental sampling.

BACKGROUND OF THE INVENTION

The following is a discussion of the relevant art, none of which is admitted to be prior art to the appended claims.

Epidemiological studies in the U.S.A. and abroad have shown associations between mortality and morbidity and human exposure to ambient particulate matter (Schartz and Dockery, *Am. Rev. Resp. Dis.* 145:600, 1992; Pope et al., *Am. Rev. Resp. Dis.* 144:668, 1992). To date, there is limited knowledge about physical or chemical property of particulate matter that are responsible for these health effects and there is an increasing interest in developing accurate measurements in the near future.

The U.S. EPA has recently recognized the need to develop continuous measurement techniques for inhalable particulate matter ($PM_{10}$ and $PM_{2.5}$). Both individual activity patterns and concentration profiles of particulate pollutants vary for time scales much shorter than 24 hours. Thus realistic exposure assessment requires sample collection over time intervals about one hour or less.

The majority of the current particulate mass measurement methods use a size selective inlet to remove particles above a certain size, usually 10 $\mu$m in diameter ($PM_{10}$) Most of the available data on $PM_{10}$ and $PM_{2.5}$, have been obtained using gravimetric methods. The collected particles, usually on Teflon filters, are weighed using microbalances under constant specified temperature and relative humidity conditions. However, gravimetric methods are not sensitive enough to measure samples for durations of less than 24 hours.

The Tapered Element Oscillating Microbalance (TEOM®) is a recently developed method that originally appeared to be very promising (Patashnick and Rupprecht, "Continuous PM-10 Measurements Using the Tapered Element Oscillating Microbalance" *J. Air Waste Manage. Assoc.* 41:1079, 1991). According to this method, the air sample is heated up to 50° C. to remove moisture, and particles are subsequently collected on a TEFLON filter that oscillates at the top of a metal rod. The amplitude of the oscillation decreases as the mass of the particles collected on the filter increases. Although this method is highly sensitive, its measurements are subject to a number of interferences; significant losses occur for semivolatile organic and inorganic compounds that in some areas can represent relatively large fraction of the total particulate matter. This problem is more pronounced for $PM_{2.5}$, which includes unstable compounds such as ammonium nitrate and carbonaceous aerosols. For areas such as California and large urban environments, this method would significantly underestimate particle mass concentrations. Also, as the composition of the air sample changes, the partitioning of air pollutants between the gas and particle phase changes, therefore absorption and/or desorption processes can take place on the filter (depending on whether the air sample becomes more or less polluted). Due to the sensitivity of the method, these phenomena can cause either negative or positive artifacts. The gains and losses of mass on the filter are a serious problem, not just of the TEOM®, but of any method that collects particles on a filter over a prolonged period of time (on the order of days). In the case of the TEOM®, the filter media are usually exposed for a week. Finally, this method presents oscillations in its response which cancel out if a large number of measurements are added to determine a multi-hour concentration estimate; however, over shorter time intervals the measurement errors due to this oscillation can exceed 20–30%.

In addition, short-term measurement of particle size distributions is at least as important as short-term measurement of total particle mass concentrations. In fact, particle size may be the most important particle parameter, since the majority of the physical processes governing the behavior of particles depend on particle size. The sources, formation mechanisms, chemical composition as well as lifetime of ambient articles greatly change with particle size. Moreover, the uptake, retention and clearance of particles by the human respiratory system depends on the particle size. Thus obtaining short-term measurements of the size distribution of ambient particles, particularly those in the accumulation mode (i.e., with aerodynamic diameters smaller than 2.5 $\mu$m) could substantially improve exposure assessment to particles and thus environmental decision making.

To date there is no adequate monitoring technique that determines the size distribution of ambient particles based on mass in short time periods. Quartz crystal piezobalances determine particulate mass indirectly through particle impaction on an oscillating quartz surface (Lundgren, D. A. In *Fine Particles*, edited by B. Y. H. Liu, Academic Press Inc., New, York, 1976; Chuan, R. L., In *Fine Particles*, edited by B. Y. H. Liu, Academic Press Inc., New, York, 1976). A quartz disk oscillates in an electric circuit at a highly stable resonant frequency which is inversely proportional to the particulate mass impacting and adhering onto the sensor. Such instruments suffer from the following potential shortcomings. First, the relationship between frequency and mass becomes non-linear for high particulate loadings. Second, since particles are collected on the crystal by impaction, the instrument response will be dependent on the sharpness of the collection efficiency and the extent of particle bounce and internal particle losses. Finally, aerosols consisting of carbonaceous particles which are composed of long stable chains of very small primary particles, cannot be determined with piezobalances. The chain aggregates contact the sensor at 2 to 3 points with most of the particulate mass waving above the sensor surface (Lundgren, D. A. and Daley, P. S., *Am. Ind. Hyg. Assoc. J.*, 581–588, 1977).

Other direct-reading methods to determine particle concentration and size distribution include optical and electrical counters. Most of the optical systems count light pulses scattered from particles that flow, one by one, through an intensely illuminated zone. One limitation is the dependence of the instrument's response on the particle refractive index (and consequently on particle composition). In addition, the smallest detectable particle size is about 0.3 $\mu$m, while much of the fine ambient particulate mass is due to particles smaller than this size. The Aerodynamic Particle Sizer (APS) (Model 3310, TSI Inc., St. Paul, Minn.; Wilson, J. C. and Liu, B. Y. H., *J. Aersol. Sci.* 11:139–150 1980; Baron, P., *Aerosol Sci. and Technol.* 5:56–67, 1985), sizes and counts particles by measuring their time-of-flight in an accelerating flow field. Particle measurement is based on particulate inertia, hence the system determines the aerodynamic particle diameter. The main shortcoming of the APS is that it cannot determine size for particles smaller than about 0.7 $\mu$m.

Electrical counters have been used to determine particle size, based on charging the sampled aerosols and measuring the ability of particles to traverse an electrical field. The most widely used instrument of this type is the Differential Mobility Analyzer (DMA) (Model 3932, TSI Inc., St. Paul, Minn.). This technology is limited to measuring ambient aerosols in the size range 0.01–0.5 µm. Using the DMA in conjunction with an optical counter or the APS would make it possible to determine a broad size range of atmospheric particles. Nevertheless, there are still three other shortcomings. First, both optical and electrical counters determine the number size distribution of particles which they subsequently convert to volume distribution. Since the density of ambient particles varies significantly (in the range of ±30% of the mean value), and since mass concentration is directly proportional to the density, large uncertainties can result from using these methods to determine particle mass concentrations as a function of size. Second, these techniques require conversion of the size distribution, by number, to a corresponding volume size distribution. The size distribution, by number, of ambient particles is dominated by ultrafine particles (i.e., smaller than 0.1 µm). The coarser the particles, the smaller their number concentration becomes. However, when converting a number to volume distribution, a 1.0 µm particle weighs as much as $10^3$ of 0.1 µm particles and $10^6$ of 0.01 µm particles. Consequently, counting errors (which are substantial for large particles, due to their relatively low number concentrations combined with electronic noise) associated with this conversion method are bound to lead to significant uncertainties in volume and consequently mass as a function of particle size. Finally, these instruments are very expensive (the combined optical/electrical counter cost is up to $100,000), with high maintenance costs, and thus are not suitable for large-scale field studies.

The U.S. EPA also recognizes the need to develop continuous measurement techniques for particle-bound water. Accurate measurement of particle-bound water is of paramount importance to the field of atmospheric chemistry, since hygroscopic ambient particles can be the media for a number of important homogeneous aqueous phase reactions. Moreover, particle water content affects particle-light interactions, and is therefore essential information for understanding and modeling visibility reduction.

To date there are no adequate monitoring techniques that measure particle-bound water. Existing techniques such as the Tandem Differential Mobility Analyzer (TDMA) (McMurry, P. H., and Stolzenburg, M. R., *Atmos. Environ.* 23:497–507, 1989) can only provide qualitative information. The TDMA method is based on the measurement of the particle size distribution before and after drying the particle sample. However, this method uses "calculations of ion strengths and molalities," based on "laboratory derived thermodynamic data for aqueous solutions of pure species." Since actual ambient particles contain variable mixtures of the different species, these calculations are imprecise. Also, most of the water is associated with particles above 0.5 microns in diameter, while DMA measurements are only accurate below this size. In addition, this method is not very sensitive because relatively large amounts of bound water can correspond to small changes in particle size due to the dependence of mass on the third power of the radius.

Direct-reading particle mass measurement methods such as the Quartz Crystal Piezoelectric Balance (QCPB) (Lundgren, D. A. In *Fine Particles,* edited by B. Y. H. Liu, Academic Press Inc., New, York, 1976) and the Tapered Element Oscillating Microbalance (TEOM®) (Pataschnick, H., and Rupprecht, E. G., *JAWMA,* 41:1079–1083, 1991), could be used to measure particle-bound water. However, these methods present some serious limitations. In the case of the QCPB method the relationship between frequency and mass becomes non-linear for high particulate loadings. In addition, since particles are collected on the crystal by impaction, the instrument response can be affected by the sharpness of the collection efficiency and the extent of particle bounce and internal particle losses. Investigators (Daley, P. S. and Lundgren, D. A., *Am. Ind. Hyg. Assoc. J.* 36:518, 1975) found that the frequency change for a given incremental mass deposit on the sensor does not remain constant as the sensor becomes loaded, due to changes in particle collection patterns over time. As previously discussed, the TEOM® method presents two serious shortcomings that make it inappropriate for measuring particle mass or any of its semi-volatile constituents such as water, ammonium nitrate, and organics. First, the sample air is heated at 50° C. to dry the particles. This can result in particle mass losses up to 60% (Hering, S. V., 6th Conference of the Intl. Soc. for Environ. Epid./4th Conference of the Intl. Soc. for Expos. Anal. (joint conference), abstract no 260, Research Park Triangle, N. C., Sep. 1994; Meyer et al., A&WMA/EPA Conference, eds. Chow, J. C. & Ono, D. M., Scotsdale, Ariz. and Pittsburgh, Pa., Jan. 1992). Second, although the monitor provides continuous measurements, it utilizes the same filter to collect particles over a long sampling period (one-week) during which semi-volatiles can be adsorbed or desorbed, depending upon changes in atmospheric concentrations and meteorological conditions. Similar artifacts in particle measurements are also expected to occur for integrated multi-hour filter samples that collect particles, although losses should be less pronounced because the air sample is not heated. Finally, a large number of studies have used sorbents downstream the particle filters to measure losses of semi-volatiles and have found that a large fraction of particulate matter is not retained by the filter. Therefore, it is not recommended that the same filter be used for collecting multi-hour samples.

A continuous ambient mass monitor (CAMM) apparatus has been developed at the Harvard School of Public Health (Abstract of presentation at conference entitled "Measurement of Toxic and Related Air Pollutants", Research Triangle Park, N. C., Cosponsored by the U.S. Environmental Protection Agency and the Air and Waste Management Association, May 7–10, 1995). This apparatus provides for the real time measurement of the amount of particulate matter in a gas and is based on the monitoring of the pressure drop across a porous membrane filter over a period of time. However, this method has been limited to the measurement of the mass of ambient fine particles (less than 2.5 µm in diameter).

SUMMARY OF THE INVENTION

The present invention concerns devices and methods that allow for continuous ambient particulate mass monitoring and ascertaining various characteristics of ambient particulate matter. The present invention enables, among other things, the monitoring of $PM_{10}$, the monitoring of coarse particles (2.5 to 10 µm), the determination of the size distribution of particles, the determination of particle density and the determination of particle-bound water. The invention also includes an automatic filter changing device and a relative humidity device that can be utilized in conjunction with the other aspects of the current invention. The invention further includes an apparatus and method for monitoring ambient particulate mass which uses a single channel.

In a first aspect, the invention features an apparatus for the continuous ambient mass monitoring of $PM_{10}$ in a gas sample, comprising a conventional inertial impactor able to remove particles larger than 10 µm in diameter in gaseous communication with the gas sample, a virtual impactor downstream of the conventional inertial impactor and in gaseous communication with gas after passage of the gas sample through the inertial impactor and able to separate the gas into a first component comprising particles less than 2.5 µm in diameter and a second component comprising particles between 2.5 µm in diameter and 10 µm in diameter, a first diffusion dryer positioned downstream of the virtual impactor through which passes the first gas component and able to reduce the relative humidity in the first gas component to 40% or lower, a second diffusion dryer positioned downstream of the virtual impactor through which passes the second gas component and able to reduce the relative humidity in the second gas component to 40% or lower, a first particulate matter collector positioned downstream of the first diffusion drier through which passes the first gas component, a second particulate matter collector positioned downstream of the second diffusion drier through which passes the second gas component, a first HEPA filtered positioned downstream of the first particulate matter collector through which passes the first gas component, a second HEPA filter positioned downstream of the second particulate matter collector through which passes the second gas component, a third particulate matter collector positioned downstream of the first HEPA filter through which passes the first gas component, a fourth particulate matter collector positioned downstream of the second HEPA filter through which passes the second gas component, a first, second, third, and fourth pressure transducer to measure differential pressure across the first, second, third, and fourth particulate matter collectors, a first pump to cause the first gas component to pass through the first and the third particulate matter collectors, and a second pump to cause the second gas component to pass through the second and the fourth particulate matter collectors.

By "gas sample" is meant atmospheric or ambient air.

By "able to remove particles larger than 10 µm in diameter" is meant that particles with size >10 µm are removed from the gas sample, while particles with size <10 µm pass through the conventional impactor, while 50% of the particles with size equal to 10 µm are removed and 50% of the particles with size equal to 10 µm pass through the conventional impactor.

By "particles less than 2.5 µm in diameter" is meant that the aerodynamic diameters of the particles are equal to or less than 2.5 µm.

By "between 2.5 µm in diameter and 10 µm in diameter" is meant that the aerodynamic diameters of the particles are between 2.5 µm and 10 µm.

By "reduce the relative humidity in the gas component to 40% or lower" is meant that when the relative humidity of the gas sample is above 40%, the system reduces the relative humidity to 40%, and when the relative humidity of the gas sample is 40% or lower, the system allows the gas sample to pass through with no further reduction in relative humidity.

By "particulate matter collector" is meant a membrane filter able to collect particulate matter in the gas sample. Preferably, the particulate matter collector is a polycarbonate track-etched membrane filter such as a Nucleopore® filter. Preferably, the first and the third particulate matter collector are different segments of one membrane filter tape and the second and the fourth particulate matter collector are different segments of another membrane filter tape.

By "HEPA filter" is meant a High Efficiency Particle Air filter which removes at least 99% of the particles from the sample gas.

By "pressure transducer" is meant a device able to detect the pressure drop across a particulate matter collector (membrane filter or its equivalent) over a period of time.

In a second aspect, the invention features a method for the continuous ambient mass monitoring of $PM_{10}$ in a gas sample, comprising the steps of providing an apparatus comprising a conventional inertial impactor able to remove particles larger than 10 µm in diameter in gaseous communication with the gas sample, a virtual impactor downstream of the conventional inertial impactor and in gaseous communication with gas after passage of the gas sample through the inertial impactor and able to separate the gas into a first component comprising particles less than 2.5 µm in diameter and a second component comprising particles between 2.5 µm in diameter and 10 µm in diameter, a first diffusion dryer positioned downstream of the virtual impactor through which passes the first gas component and able to reduce the relative humidity in the first gas component to 40% or lower, a second diffusion dryer positioned downstream of the virtual impactor through which passes the second gas component and able to reduce the relative humidity in the second gas component to 40% or lower, a first particulate matter collector positioned downstream of the first diffusion drier through which passes the first gas component, a second particulate matter collector positioned downstream of the second diffusion drier through which passes the second gas component, a first HEPA filter positioned downstream of the first particulate matter collector through which passes the first gas component, a second HEPA filter positioned downstream of the second particulate matter collector through which passes the second gas component, a third particulate matter collector positioned downstream of the first HEPA filter through which passes the first gas component, a fourth particulate matter collector positioned downstream of the second HEPA filter through which passes the second gas component, a first, second, third, and fourth pressure transducer to measure differential pressure across the first, second, third, and fourth particulate matter collectors, a first pump to cause the first gas component to pass through the first and the third particulate matter collectors, and a second pump to cause the second gas component to pass through the second and the fourth particulate matter collectors, causing the gas to pass to the first, second, third, and fourth particulate matter collectors, and measuring the pressure differential between the first and third particulate matter collectors and the second and fourth particulate matter collectors as a basis for determining the amount of $PM_{10}$ in the gas.

In a third aspect, the invention features an automatic filter changing mechanism comprising a single continuous strip of particulate matter collector tape through which sample air and particle-free air are simultaneously passed in separate channels, a means for sealing the separate channels with the particle matter collector tape, porous metal disks supporting the particle matter collector tape, a supply reel, and a roller controlled with a stepping motor so as to advance the particle matter collector tape by a fixed amount.

By "particle matter collector tape" is meant a strip of membrane filter able to collect particulate matter. Preferably, the particulate matter collector tape comprises a polycarbonate track etched membrane filter such as a Nucleopore® filter.

By "sample air" is meant atmospheric or ambient air. The portion of the particulate matter collector tape through which passes the sample air represents the first particulate matter collector in the single channel device (see below). The sample air includes air that has passed through a conventional impactor and/or a virtual impactor.

By "particle free air" is meant sample gas from which at least 99% of the particles have been removed using a High Efficiency Particle Air filter (HEPA filter). The portion of the particulate matter collector tape through which passes the particle free air represents the second particulate matter collector in the single channel device (see below).

By "means for sealing" is meant a flexible washer (e.g., plastic) above the collector tape and a second washer below the collector tape, and a mechanism for pressing the two washers together so as to allow the sample gas to pass through the collector tape without leaking and without distorting the shape of the collector tape.

By "porous metal disks" are meant disks, such as those made of sintered stainless steel, which provide a support surface for the collector tape and allow the sample gas to pass through.

By "supply reel" is meant a spool or other means for containing rolled-up or packaged collector tape which is unrolled or unpackaged and supplied step-wise as successive segments of collector tape are sealed and unsealed as they are exposed to particle free air and sample air.

By "roller controlled with a stepping motor" is meant a spool or other surface upon which collector tape is rolled up or collected after it passes through the sealing mechanism, which is controlled by a stepping motor so that successive segments of collector tape are advanced periodically.

In a fourth aspect, the invention features a relative humidity control unit comprising: a semi-permeable membrane tube through which sample air flows which is positioned concentric to an outer tube through which dry air flows, a container of silica gel through which the dry air flows after passing around the semi-permeable membrane tube, a filter positioned downstream of the container of silica gel, a pump positioned downstream of the silica gel, a second filter positioned downstream of the pump, and a valve positioned downstream of the second filter such that the dry air is able to return to the outer tube.

By "semi-permeable membrane tube" is meant a membrane tube which allows water vapor to pass through, while other gases are not affected. For example the tube can be constructed from a Nafion® membrane.

In a fifth aspect, the invention features a single channel apparatus for measuring the amount of particulate matter in a gas sample, comprising a first particulate matter collector in gaseous communication with the gas sample, a HEPA filter positioned downstream from the first particulate matter collector, a second particulate matter collector positioned downstream of the HEPA filter, a first pressure transducer to determine the pressure drop across the first particulate matter collector, a second pressure transducer to determine the pressure drop across the second particulate matter collector, and a pump to cause gas to pass from the gas sample to the first particulate matter collector, the HEPA filter and the second particulate matter collector.

The pressure drop across the first particulate matter collector represents the total pressure drop caused by the passage of the gas sample (due to the particulate matter in the gas sample collecting on the particulate matter collector and due to changes in flow, temperature, and humidity). The pressure drop across the second particulate matter collector represents the pressure drop due to changes in flow, temperature, and humidity as prior contact with the HEPA filter has removed at least 99% of the particulate matter from the gas. By subtracting the pressure drop across the second particulate matter collector from the pressure drop across the first particulate matter collector the ambient particle mass concentration in the gas sample can be determined as the pressure drop is a linear function of the particle mass concentration of the gas sample.

As previously discussed, the first and the second particulate matter collectors are preferentially different segments of the same membrane filter tape.

In a sixth aspect, the invention features a single channel method for measuring the amount of particulate matter in a gas sample, comprising the steps of providing an apparatus comprising a first particulate matter collector in gaseous communication with the sample gas, a HEPA filter positioned downstream from the first particulate matter collector, a second particulate matter collector positioned downstream of the HEPA filter, a first pressure transducer to determine the pressure drop across the first particulate matter collector, a second pressure transducer to determine the pressure drop across the second particulate matter collector, and a pump to cause gas to pass from the gas sample to the first particulate matter collector, the HEPA filter and the second particulate matter collector and causing the gas sample to pass to the first and the second particulate matter collectors, and measuring the pressure differential between the first and the second particulate matter collectors as a basis for determining the amount of particulate matter in the gas sample.

In a seventh aspect, the invention features an apparatus for measuring the mass concentration of ambient particles in a gas sample as a function of the particle size, comprising a conventional impactor with a 10 $\mu$m cutpoint, a virtual impactor with a 2.5 $\mu$m cutpoint positioned downstream from the conventional impactor so as to separate the gas sample into a first gas component comprising particles with a size range of aerodynamic diameter of $\leq 2.5$ $\mu$m and into a second gas component comprising particles with a size range between 2.5 and 10 $\mu$m, a first channel positioned downstream from the virtual impactor containing a conventional impactor with a size cutoff of 0.15 $\mu$m so that upon passage of a first portion of the first gas component through the conventional impactor particles that remain in the channel comprise a size range of aerodynamic diameter of $\leq 0.15$ $\mu$m, a second channel positioned downstream from the virtual impactor containing a conventional impactor with a size cutoff of 0.3 $\mu$m so that upon passage of a second portion of the first gas component through the conventional impactor particles that remain in the channel comprise a size range of aerodynamic diameter of $\leq 0.3$ $\mu$m, a third channel positioned downstream from the virtual impactor containing a conventional impactor with a size cutoff of 0.6 $\mu$m so that upon passage of a third portion of the first gas component through the conventional impactor particles that remain in the channel comprise a size range of aerodynamic diameter of $\leq 0.6$ $\mu$m, a fourth channel positioned downstream from the virtual impactor containing a conventional impactor with a cutoff of 1.0 $\mu$m so that upon passage of a fourth portion of the first gas component through the conventional impactor particles that remain in the channel comprise a size range of aerodynamic diameter of $\leq 1.0$ $\mu$m, a fifth channel so that upon passage of a fifth portion of the first gas component through the channel particles that remain in the channel comprise a size range of aerodynamic diameter of $\leq 2.5$ $\mu$m, a sixth channel positioned downstream from the virtual impactor containing a conventional impactor with a cutoff of 5.0 $\mu$m so that upon passage of a first portion of the second gas component through the channel the particles in the channel comprise a size range of aerodynamic diameter of 2.5 to 5.0 $\mu$m, a seventh channel positioned downstream from the virtual impactor so that so that upon passage of a second portion of the second gas component through the channel particles in the channel comprise a size range of aerodynamic diameter of 2.5 to 10.0 µm, a set of diffusion dryers positioned downstream of the impactors in the channels, a first particulate matter collector positioned downstream of the diffusion dryer for each channel, a HEPA filter positioned downstream of the first particulate matter collector for each channel, a second particulate matter collector positioned downstream of the HEPA filter for each channel and a first and second pressure transducer for each channel for measuring the pressure drop per unit time across the first and second particulate matter collectors, and a pump located downstream of the second particulate matter collector for each channel to cause the portion of the first or the second gas component of the gas sample to pass to the first and the second particulate matter collectors.

By "10 µm cutpoint" is meant that particles with size >10 µm are removed from the gas sample, while particles with size <10 µm pass through the conventional impactor, while 50% of the particles with size equal to 10 µm are removed from the gas sample and 50% of the particles with size equal to 10 µm pass through the conventional impactor.

By "2.5 µm cutpoint" is meant that particles with size >2.5 µm are removed from the sample gas, while particles with size <2.5 µm pass through the virtual impactor, while 50% of the particles with size equal to 2.5 µm are removed and 50% of the particles with size equal to 2.5 µm pass through.

By "size range of aerodynamic diameter of ≦2.5 µm" is meant that particles comprise a size range equal to or less than 2.5 µm.

By "size range between 2.5 and 10 µm" is meant particles which have sizes equal to or greater than 2.5 µm and equal to or less than 10 µm.

By "size cutoff of 0.15 µm" is meant that particles with size >0.15 µm are removed from the first gas component, while particles with size <0.15 µm pass through the conventional impactor, while 50% of the particles equal to 0.15 µm are removed and 50% of the particles equal to 0.15 µm pass through.

By "size cutoff of 0.3 µm" is meant that particles with size >0.3 µm are removed from the first gas component, while particles with size <0.3 µm pass through the conventional impactor, while 50% of the particles equal to 0.3 µm are removed and 50% of the particles equal to 0.3 µm pass through.

By "size cutoff of 0.6 µm" is meant that particles with size >0.6 µm are removed from the first gas component, while particles with size <0.6 µm pass through the conventional impactor, while 50% of the particles equal to 0.6 µm are removed and 50% of the particles equal to 0.6 µm pass through.

By "size cutoff of 1.0 µm" is meant that particles with size >1.0 µm are removed from the first gas component, while particles with size <1.0 µm pass through the conventional impactor, while 50% of the particles equal to 1.0 µm are removed and 50% of the particles equal to 1.0 µm pass through.

By "size cutoff of 5.0 µm" is meant that particles with size >5.0 µm are removed from the second gas component, while particles with size <5.0 µm pass through the conventional impactor, while 50% of the particles equal to 5.0 µm are removed and 50% of the particles equal to 5.0 µm pass through.

By "size range of aerodynamic diameter of 2.5 to 10.0 µm" is meant that particles have a size range between 2.5 µm and 10.0 µm.

In an eighth aspect, the invention features a method for measuring the mass concentration of ambient particles in a gas sample as a function of the particle size, comprising the steps of providing an apparatus comprising a conventional impactor with a 10 µm cutpoint, a virtual impactor with a 2.5 µm cutpoint positioned downstream from the conventional impactor so as to separate the gas sample into a first gas component comprising particles with a size range of aerodynamic diameter of ≦2.5 µm and into a second gas component comprising particles with a size range between 2.5 and 10 µm, a first channel positioned downstream from the virtual impactor containing a conventional impactor with a size cutoff of 0.15 µm so that upon passage of a first portion of the first gas component through the conventional impactor particles that remain in the channel have a size range of aerodynamic diameter of ≦0.15 µm, a second channel positioned downstream from the virtual impactor containing a conventional impactor with a size cutoff of 0.3 µm so that upon passage of a second portion of the first gas component through the conventional impactor particles that remain in the channel have a size range of aerodynamic diameter of≦0.3 µm, a third channel positioned downstream from the virtual impactor containing a conventional impactor with a size cutoff of 0.6 µm so that upon passage of a third portion of the first gas component through the conventional impactor particles that remain in the channel have a size range of aerodynamic diameter of ≦0.6 µm, a fourth channel positioned downstream from the virtual impactor containing a conventional impactor with a cutoff of 1.0 µm so that upon passage of a fourth portion of the first gas component through the conventional impactor particles that remain in the channel have a size range of aerodynamic diameter of ≦1.0 µm, a fifth channel so that upon passage of a fifth portion of the first gas component through the conventional impactor particles that remain in the channel have a size range of aerodynamic diameter of ≦2.5 µm, a sixth channel positioned downstream from the virtual impactor containing a conventional impactor with a cutoff of 5.0 µm so that upon passage of a first portion of the second gas component through the conventional impactor particles that remain in the channel have a size range of aerodynamic diameter of 2.5 to 5.0 µm, a seventh channel positioned downstream from the virtual impactor so that so that upon passage of a second portion of the second gas component through the channel particles in the channel have a size range of aerodynamic diameter of 2.5 to 10.0 µm, a set of diffusion dryers positioned downstream of the impactors in the channels, a first particulate matter collector positioned downstream of the diffusion dryer for each channel, a HEPA filter positioned downstream of the first particulate matter collector for each channel, a second particulate matter collector positioned downstream of the HEPA filter for each channel, a first and second pressure transducer for each channel for measuring the pressure drop per unit time across the first and second particulate matter collectors, a pump located downstream of the second particulate matter collector for each channel to cause the portion of the first or the second gas component of the gas sample to pass to the first and second particulate matter collectors and causing the portions of the first and the second gas components to pass to the first and the second particulate matter collectors of the channels and measuring the pressure differential between the first and the second particulate matter collectors for each channel as a basis for determining the mass concentration of ambient particles in the gas sample as a function of particle size.

In a ninth aspect, the invention features an apparatus for measuring particle-bound water and particle density in ambient particles in a gas sample, comprising a 10 μm cutpoint conventional impactor for removing particles larger than 10 μm from the gas sample, a virtual impactor with a 2.5 μm cutpoint positioned downstream from the conventional impactor so as to separate the gas sample into a first gas component comprising particles with a size range of aerodynamic diameter of ≦2.5 μm and into a second gas component comprising particles with a size range between 2.5 and 10 μm, a first channel positioned downstream of the virtual impactor for passage of a first portion of the first gas component and a second channel with a diffusion drier positioned downstream of the virtual impactor for passage of a second portion of the first gas component, a third channel positioned downstream of the virtual impactor for passage of a first portion of the second gas component and a fourth channel with a diffusion drier positioned downstream of the virtual impactor for passage of a second portion of the second gas component, a set of three particulate matter collectors arranged in series and positioned downstream of the diffusion drier in the second and the fourth channels and positioned downstream of the virtual impactor in the first and third channels, a HEPA filter positioned downstream of the three particulate matter collectors in each channel, a fourth particulate matter collector positioned downstream of the HEPA filter in each of the channels, a first, second, third, and fourth pressure transducer for measuring the pressure drop across each particulate matter collector located in each channel, and a pump positioned downstream of the fourth particulate matter collector for each of the channels to cause the first or second portion of the first or the second gas component to pass to the first, second, third, and fourth particulate matter collectors in each channel.

By "particle-bound water" is meant water molecules which are associated with ambient air particles and are either absorbed, adsorbed, or in liquid phase.

By "particle density in ambient particles" is meant the average density of particles contained in sample air, including the contribution to the average density of those particles which contain particle-bound water.

In a tenth aspect, the invention features a method for measuring particle-bound water, and particle density in ambient particles contained in a gas sample, comprising the steps of providing an apparatus comprising a 10 μm cutpoint conventional impactor for removing particles larger than 10 μm from the gas sample, a virtual impactor with a 2.5 μm cutpoint positioned downstream from the conventional impactor so as to separate the gas into a first gas component comprising particles with a size range of aerodynamic diameter of ≦2.5 μm and into a second gas component comprising particles with a size range between 2.5 and 10 μm, a first channel positioned downstream of the virtual impactor for passage of a first portion of the first gas component and a second channel with a diffusion drier positioned downstream of the virtual impactor for passage of a second portion of the first gas component, a third channel positioned downstream of the virtual impactor for passage of a first portion of the second gas component and a fourth channel with a diffusion drier positioned downstream of the virtual impactor for passage of a second portion of the second gas component, a set of three particulate matter collectors, arranged in series and positioned downstream of the diffusion drier in the second and fourth channels and positioned downstream of the virtual impactor in the first and third channels, a HEPA filter positioned downstream of the three particulate matter collectors in each channel, a fourth particulate matter collector positioned downstream of the HEPA filter in each channel, a first, second, third, and fourth pressure transducer for measuring the pressure drop across each particulate matter collector for each channel, and a pump positioned downstream of the fourth particulate matter collector for each of the channels to cause the first or the second portion of the first or the second gas component to pass to the first, second, third, and fourth particulate matter collectors in each of the channels, and causing the first and the second portion of the first and the second gas component to pass to the first, second, third, and fourth particulate matter collector in the channels, and measuring the pressure differential between the first, second, third, and fourth particulate matter collector in each channel as a basis for determining the particle-bound water and particle density in ambient particles contained in the gas sample.

Other features and advantages of the invention will be apparent from the following description of the preferred embodiments thereof, and from the claims.

BRIEF DESCRIPTION OF THE FIGURES

FIG. 1 is schematic design of the apparatus utilized for continuous ambient mass monitoring of $PM_{10}$.

FIG. 2 is a schematic of the automatic filter changing mechanism.

FIG. 3 is a schematic diagram of the relative humidity control unit.

FIG. 4 is a schematic diagram of the single channel apparatus for continuous ambient mass monitoring.

FIG. 5 is a schematic diagram of the apparatus for measurement of mass concentration of ambient particles as a function of particle size.

FIG. 6 is a schematic diagram of the apparatus which determines particle density and particle-bound water.

DESCRIPTION OF THE PREFERRED EMBODIMENTS

The following Examples are provided for further illustrating various aspects of the invention and are in no way intended to be limiting of the scope.

EXAMPLE 1

Measurement of Coarse Particles

Applicants have discovered that by utilizing the appropriate pore diameters and sampling flow rates, monitoring of the pressure drop across a particulate matter collector such as a Nucleopore® filter could allow for the measurement of "coarse" particles (sizes 2.5 to 10 μm).

The relationship between the pressure drop across a Nucleopore® membrane filter and the aerosol mass concentration was investigated in laboratory experiments for particles in the size range 2.5–10.0 μm. Artificial aerosols comprising monodisperse fluorescent polystyrene latex particles (PSL) in the following sizes: 2.9, 4.2, 5.4, 6.5, and 10.0 μm were utilized. In addition to monodisperse fluorescent particles, polydisperse iron oxide particles (size range 1–10 μm) and glass beads (size range 2–10 μm) were used as the test aerosol.

For a first study, a 12 μm pore diameter Nuclepore® filter operating at sampling flow rates of 1 and 3 liters/minute was chosen. The results from these experiments are shown in Table 1. The experimentally measured collection efficiency values for the Nuclepore® filter are also shown in this table. At a flow rate of 3 liters/minute, the pressure drop per unit time and concentration depends strongly on the particle size.

More specifically, the pressure drop per unit time and loading, decrease from $16.5 \cdot 10^{-6}$ inches of $H_2O/\mu g/m^3$ per hour to $2.1 \cdot 10^{-6}$ inches of $H_2O/\mu g/m^3$ per hour as the particle size increases from 4.2 to 9.5 $\mu m$. The reason for this decrease in the pressure drop is impaction of the larger size particles on the inter pore surface of the filter. Particles collected on this surface do not contribute to the increase in the pressure drop with loading.

A second series of experiments was conducted, with a pore size of 10 $\mu m$ and a flow rate of 1 liter/minute. The results in Table 1 show that this reduction in the flow rate made the pressure drop per unit time per unit concentration independent of the particle size. For this pore size and flow this value is 7.3 ($\pm 0.6$)$\cdot 10^{-6}$ inches of $H_2O/\mu g \cdot m^{-3}$ per hour. Thus, particles are collected by the filter almost exclusively by deposition on the pore edges due to interception.

To investigate the possibility of increasing the pressure drop per unit time and concentration value, and thereby to increase the sensitivity of the mass measurement technique, the flow rate was increased to 1.5 liters/minute. Results from these experiments are shown in Table 2. At 1.5 liters/minute, the value of the pressure drop per unit time and concentration is 9.5 ($\pm 0.5$)$\cdot 10^{-6}$, and independent of the particle size. This value is approximately 1.3 times higher than that at a flow rate of 1 liter/minute, and roughly equals the ratio of the flow rates. The independence of this value on the particle size suggests that particle impaction on the inter-pore filter surface was minimized. The absence of impaction onto the interpore surface was confirmed by examining the filters with a microscope after each experiment. Even large particles, comparable to the pore size (10 $\mu m$ in diameter) deposited almost exclusively on the edges of the filter pores, causing an increase in the pressure drop due to partial obstruction to the fluid flow.

In order to investigate the effect of particle density on the value of pressure drop per unit time and concentration, polydisperse aerosols of iron oxide particles (density 1.6 g/cm$^3$, size range 1–10 $\mu m$) and glass beads (density 2.6 g/cm$^3$, size range 2–10 $\mu m$) were generated, and the results are shown in Table 2. The pressure drop per unit time and concentration was $8.5 \cdot 10^{-6}$ and 6.1 ($\pm 0.1$)$\cdot 10^{-6}$ inches of $H_2O/\mu g/m^3$ per hour for iron oxide and glass bead particles, respectively. Theoretical analysis predicts that the increase in the pressure drop per unit time and concentration should be proportional to the square root of particle density. This is because the collection efficiency on the pore edges depends on the particle aerodynamic diameter, which is defined as the product of the particle physical diameter times the square root of particle density. Table 3 shows the pressure drop per unit time and concentration for all three types of particles, including actual average values and values normalized for density. It is clear that the values normalized for particle density agree within experimental error for all three types.

TABLE 1

Coarse Particle Mass Monitoring

| Pore Size ($\mu m$) | Particle Size and Type | Sampling flow Rate (LPM) | Filter Collection Efficiency (%) | $\Delta P/c_m/t (\times 10^{-6})$ (inches $H_2O/\mu g/m^3$ per hr)$^\S$ |
|---|---|---|---|---|
| 12 | 4.2 $\mu m$ PSL | 3 | 56.2 | 16.5 |
| 12 | 4.2 $\mu m$ PSL | 3 | 43.3 | 14.0 |
| 12 | 6.5 $\mu m$ PSL | 3 | 64.3 | 7.5 |
| 12 | 6.5 $\mu m$ PSL | 3 | 59.6 | 8.5 |
| 12 | 9.5 $\mu m$ PSL | 3 | 92.1 | 2.1 |

TABLE 1-continued

Coarse Particle Mass Monitoring

| Pore Size ($\mu m$) | Particle Size and Type | Sampling flow Rate (LPM) | Filter Collection Efficiency (%) | $\Delta P/c_m/t (\times 10^{-6})$ (inches $H_2O/\mu g/m^3$ per hr)$^\S$ |
|---|---|---|---|---|
| 10 | 10.0 $\mu m$ PSL | 1 | 95.1 | 7.1 |
| 10 | 10.0 $\mu m$ PSL | 1 | 97.0 | 6.5 |
| 10 | 6.2 $\mu m$ PSL | 1 | 54.3 | 6.3 |
| 10 | 6.2 $\mu m$ PSL | 1 | 60.3 | 7.2 |
| 10 | 4.2 $\mu m$ PSL | 1 | 39.3 | 7.8 |
| 10 | 2.9 $\mu m$ PSL | 1 | 34.5 | 7.8 |
| 10 | 2.9 $\mu m$ PSL | 1 | 33.7 | 8.0 |

$^\S$Pressure drop per unit time and mass concentration.

TABLE 2

Coarse Particle Mass Monitoring at 1.5 LPM sampling flow rate.

| Pore size ($\mu m$) | Particle Size and Type | Mass Concentration ($\mu g/m^3$) | Filter Collection Efficiency (%) | $\Delta P/c_m/t (\times 10^{-6})$ (inches $H_2O/\mu g/m^3$ per hr)$^\S$ |
|---|---|---|---|---|
| 10 | 10 $\mu m$, PSL | 198.0 | 98.7 | 9.0 |
| 10 | 9.2 $\mu m$, PSL | 98.3 | 99.3 | 8.8 |
| 10 | 9.2 $\mu m$, PSL | 119.2 | 99.9 | 10.3 |
| 10 | 6.3 $\mu m$, PSL | 129.0 | 56.8 | 9.2 |
| 10 | 5.4 $\mu m$, PSL | 166.6 | 49.1 | 9.1 |
| 10 | 4.2 $\mu m$, PSL | 198.1 | 42.5 | 9.6 |
| 10 | 3.0 $\mu m$, PSL | 261.3 | 33.7 | 10.5 |
| 10 | Iron Oxide 1–10 $\mu m$; $\rho_p$ = 1.6 g/cm$^3$ | 228.5 | NA | 8.5 |
| 10 | Glass Beads, 2–10 $\mu m$, $\rho_p$ = 2.6 g/cm$^3$ | 138.4 | NA | 6.1 |
| 10 | Glass Beads, 2–10 $\mu m$, $\rho_p$ = 2.6 g/cm$^3$ | 89.6 | NA | 6.1 |
| 10 | Glass Beads, 2–10 $\mu m$, $\rho_p$ = 2.6 g/cm$^3$ | 111.1 | NA | 5.7 |
| 10 | Glass Beads, 2–10 $\mu m$, $\rho_p$ = 2.6 g/cm$^3$ | 142.8 | NA | 6.6 |

$^\S$Pressure drop per unit time and mass concentration.

TABLE 3

Pressure drop per unit time and concentration normalized for particle density.

| Particle type | Particle Density (g/cm$^3$) | Average $\Delta P/c_m/t$ ($\times 10^{-5}$) (inches $H_2O/\mu g/m^3$ per hr)$^\S$ | Normalized $\Delta P \cdot (\rho_p)^{0.5}/c_m/t$ ($\times 10^{-6}$) |
|---|---|---|---|
| PSL | 1.05 | 9.5 ($\pm 0.6$) | 9.7 |
| Iron Oxide | 1.6 | 8.5 | 10.3 |
| Glass beads | 2.6 | 6.1 ($\pm 0.1$) | 9.8 |

EXAMPLE 2

PM$_{10}$ Measurement

PM$_{10}$ is calculated from the sum of the coarse and the fine mass concentrations. The apparatus and method of the instant invention simultaneously measures the two components of PM$_{10}$, fine mass (size below 2.5 $\mu m$, PM$_{2.5}$) and coarse mass (size between 2.5 and 10 $\mu m$). First, particles larger than 10 μm are removed by a conventional inertial impactor. Then, fine and coarse particles are separated using a virtual impactor, which concentrates the coarse particles. By increasing the concentration of coarse particles, the system provides additional sensitivity which is necessary for measuring these particles by the pressure drop across a filter. Next, the relative humidity is reduced to 40% (or lower) to dry both types of aerosol particles. Finally, the mass concentration of each component is measured separately, using the filter pressure drop method. It is necessary to measure the mass concentration of both the minor flow of the virtual impactor, containing all of the coarse particles and a relatively small fraction of $PM_{2.5}$ and to measure the concentration of the major flow, containing only $PM_{2.5}$.

For the measurement of the components of $PM_{10}$ two parameters that must be optimized are pore size and flow rate. The basic principle for these parameters is to use the smallest possible pore size and the highest flow rate. The smaller the pore size, the greater the pressure drop per unit mass concentration per unit time. Inversely, the higher the flow rate, the greater the pressure drop per unit mass concentration per unit time. For fine particles a pore size of 2 μm is the smallest that can be used, as this is the smallest appropriate manufactured size. For coarse particles, the smallest pore size is 10 μm. The optimum flow rates for fine and coarse particles are different. The limiting factor for increasing the flow to get the highest sensitivity is that the particles can get enough inertia to impact on the interpore surface of the filter. When the particles impact, they are unavailable to be intercepted on the edges of the pores, and consequently cannot contribute to the increase in pressure drop across the filter. Moreover, the fraction of particles that are impacted is strongly dependent on particle size. For each size range, fine and coarse, there is an optimum flow rate which is determined experimentally by two tests. These tests are performed using particles near the largest size of each range, 2 μm diameter for fine mass, and 10 μm diameter for coarse mass. The first test is to find the highest flow rate which produces negligible impaction on the inter-pore surface of the filter. This is done using light microscopy to examine the filters directly. The second test is to determine whether the pressure drop vs concentration is independent of particle size. The highest flow that satisfies both of these tests is the optimum flow rate, yielding the maximum sensitivity.

Measurement of fine particles can be carried out using the Continuous Ambient Mass Monitor (CAMM) method. However, this method cannot be utilized to measure coarse particles. For the measurement of coarse particles a virtual impactor is required. In the virtual impactor, the sample gas containing both coarse and fine particles is accelerated through a nozzle. Directly downstream of the acceleration nozzle is a collection nozzle ("receiving tube"). A small fraction of the gas passes through the collection nozzle (minor flow), while most of the gas bypasses the collection nozzle (major flow). With an appropriate velocity through the acceleration nozzle, all of the larger particles have enough momentum to pass straight through into the collection nozzle. Thus, the major flow of the sample gas which bypasses the collection nozzle contains only fine particles, while the minor flow of the gas which passes through the collection nozzle contains both coarse and fine particles. However, the concentration (number of particles per unit volume) of the fine particles in the major flow is the same as in the original sample gas, while the concentration of the coarse particles in the minor flow is multiplied by the ratio of the total flow to the minor flow. The concentration of fine particles in the minor flow is the same as in the major flow, since these particles don't have enough momentum to be segregated by the acceleration and collection nozzles. The mass concentration of fine particles in both the minor and major flows are measured independently, using separate filter pressure drop systems. The mass concentration of the fine particles is that which is measured for the major flow. The mass concentration of the coarse particles is determined based on the minor flow (taking into account the ratio of total to minor flow), but requires a correction due to the simultaneous presence of the fine particles.

A schematic of the design of the apparatus for the continuous ambient mass monitoring of $PM_{10}$ is shown in FIG. 1. The air sample is first drawn through a conventional inertial impactor (1) to remove particles larger than 10 μm. Subsequently the sampled aerosol is drawn through a virtual inertial impactor (2) with a 50% cutpoint at 2.5 μm. The minor flow of the virtual impactor (typically 2–10% of the total flow entering the virtual impactor) contains all the coarse particles (size between 2.5 and 10 μm), concentrated by a factor equal to the ratio of the total-to-minor flow, along with the original ambient concentration of $PM_{2.5}$ particles (size below 2.5 μm). The major flow (90–98% of the total, adjustable to vary the sensitivity for coarse mass concentration) contains only fine particles.

Mass measurements are made as follows: The minor flow of the virtual impactor, containing all the coarse particles, is drawn first through a diffusion dryer (3) which reduces the relative humidity to 40% (or less), to produce dried particles. The coarse mass concentration is then measured by monitoring the pressure drop across a particulate matter collector (e.g., a filter) as a function of time. This system typically consists of a first position on a first Nucleopore® membrane filter tape with a filter changing mechanism (4), a first pressure transducer (e.g., a high sensitivity transducer (range 0–1 inches $H_2O$, accuracy=0.25% FS) (5), a HEPA filter (6), a second position on the first Nucleopore® membrane filter tape (7), a second pressure transducer (8), a vacuum pump (9), and a data acquisition system (e.g., generally, the pressure transducers are connected to a signal processor, which is a multichannel digital-to-analog converter and a signal display, that stores and displays all signal inputs) (10). The major flow of the virtual impactor, containing fine particles, is also passed through a diffusion dryer (11) and then drawn through a first position on a second Nucleopore® membrane filter tape with a filter changing mechanism (12), a first pressure transducer (13), a HEPA filter (14) a second position on the second Nucleopore® membrane filter tape (15), a second pressure transducer (16), and a vacuum pump (17)).

For both particle sizes, the sampled particles are dried after and not before the virtual impactor so that particles entering the two channels are classified at ambient humidity, while the mass measurements correspond to dried particle mass (with the contribution to mass from particle-bound water removed). This is in accordance with the U.S. EPA reference method for $PM_{10}$, which requires that sample filters containing collected particulate matter be equilibrated at a relative humidity of 40% or less prior to gravimetric determination of particle mass concentration. If particles were dried prior to the size separation by the virtual impactor, the measured size distribution would be different from the ambient size distribution, due to shrinking of water-containing particles.

$PM_{10}$, is determined by summing the concentrations for coarse mass (size between 2.5 and 10.0 μm) and fine mass ($PM_{2.5}$). Since the minor flow which contains concentrated coarse particles also contains a relatively small amount of fine particles at ambient concentration, the direct mass measurement for coarse mass obtained from the minor flow must be corrected, proportionately, for the contribution of fine particles that it contains (the calculation method for making this correction is discussed in the Data Reduction section (see below)),

EXAMPLE 3

Automatic Filter Changing Mechanism

This automatic filter changing mechanism is computer-controlled to seal, unseal, and advance the position of the filter tape, i.e., a narrow strip of membrane filter (particulate matter collector), such as a Nucleopore® filter membrane. The tape can be advanced at fixed time intervals (e.g. 30 min), or at intervals which depend on the total amount of particle loading at the given tape position. Both laboratory and ambient air tests using the tape system indicated that this system produces pressure drop measurements of high consistency, and provides adequate sensitivity.

The automatic filter changing mechanism is shown schematically in FIG. 2. Sample air (1) and particle-free air (2) are simultaneously passed through a single continuous tape strip of Nucleopore® filter membrane (3). The sample air is air that has passed through a conventional and/or virtual impactor. The particle free air is air that has passed through a HEPA filter. To seal each path securely, the lower section of the mechanism is raised to compress polyurethane washers (4) for both channels. The system is designed to position the lower section precisely, each time the seal is made. This creates the same amount of tension on the seals every time a new section of filter is used. The result is that the there is a very reproducible conformation of the filter membrane for each of the two paths. This feature is very important because excessive variability in this conformation would cause decreased reproducibility in the mass concentration derived from the pressure drops across the two paths.

For both paths, physical support for the filter tape is provided by porous metal disks (5). These disks are removable for periodic cleaning and replacement. This is an important feature because the particles which pass through the filter membrane will slowly collect in the porous metal disks. If these particles were allowed to block a significant fraction of the path through the disk, the effective face velocity of the sample air through the disk would be increased. This would alter the relation between pressure drop and particle mass concentration, resulting in biased particle mass measurements. The pores in the disks are large enough so that only infrequent maintenance is required. A computer program can be used to operate the system which allows the total integrated mass collected to be constantly monitored. Remote access to the computer data makes it possible to have off-site notification of when it is necessary to change the support disks, based on a predetermined maximum allowed value for integrated mass.

The tape drive component of the automatic filter changing system contains a stepping motor which is attached to a roller (6) to precisely advance the filter tape by a fixed amount. The supply reel (7) of unexposed filter tape has constant friction to maintain a uniform tension on the tape, prior to each time the seal is closed. This feature plays the same role as described above for the constant compression of the seal, i.e., it also helps assure maximum reproducibility in the conformation of the sealed area of the filter, providing optimum reproducibility of mass concentration measurements.

Experimentally it has been shown that the relation between the pressure drop change and the fine particle mass concentration is only linear for a loading of up to about 65 $\mu g/M^3 \cdot hr$ (i.e., a time weighted average of mass concentration times number of hours). When the ambient concentration is 65 $\mu g/M^3$ or less, the system can be operated in a mode which advances the tape once an hour, or more frequently. If the concentration is 130 $\mu g/^3$, then the tape must be advanced every half hour. Since the mass concentration is continuously measured it is possible to automatically advance the tape when higher concentrations occur, so that the maximum loading is never exceeded. When the system is operated in this mode, the time required for the total length of filter tape to be used up will vary. However, since a computer can keep track of the number of times the tape has been advanced, remote off-site access to this information allows the operator to determine when the tape needs to be replaced.

EXAMPLE 4

Relative Humidity Control Unit

A relative humidity control unit is used to adjust the relative humidity (RH) of the sample air to 40% or less. The key component of the control unit is a semi-permeable membrane which allows water vapor to pass through, while other gases are not affected, e.g. a Nafion® membrane. The reduction in RH of the air dries the ambient particles, appropriately reducing their size for the subsequent mass concentration measurement using the pressure drop across a particulate matter collector, e.g., a membrane filter such as Nucleopore® filter. Dry air flows on the outside of the Nafion® tube, while sample air flows through the inside. When the ambient RH is 40% (or some other preselected value) or higher, the flow of dry air is automatically adjusted to change the sample RH to 40%, using a feedback system, based on measurement of RH downstream in the pressure drop system. When the ambient RH is below 40% (or some other preselected value), the dry air flow is stopped, so that the sample air RH is the same as ambient.

A schematic diagram of the relative humidity control unit is shown in FIG. 3. The Nafion® membrane tube (1) is concentric with a larger tube (2) used for the dry air flow. The length of the Nafion® tube is chosen to be adequate to achieve the desired RH change in the sample air, based on the sample air flow and the efficiency per unit length of the membrane. The actual length is increased to account for degradation of this efficiency during use, so that the effective use life is at least one month for continuous operation.

The pump (3) used to supply the dry air (produced by passage through silica gel (4)) has a variable flow rate. This flow is proportionate to the applied voltage, which is determined by a feedback system. The feedback system uses a probe downstream from the pressure drop measurement component of the system in which it is employed to determine the RH of the air achieved by the drying system. Thus the RH is maintained at 40% (or some other pre-selected value) for all times when ambient RH is above 40%. In order to not dry the sample air more than is needed, the pump is automatically turned off when ambient RH is 40% or lower. Filter (5) removes particles that could come from the silica gel container and that could interfere with the pump. A second filter (6) removes any particles that may have formed within the pump so that they do not clog the valve (7) and also so that they do not contaminate the outer surface of the Nafion® membrane. Valve (7) is adjusted so that the range of flows produced by varying the voltage to the pump achieves a maximum control of relative humidity (RH), because the pump has more capacity for flow than the maximum flow needed to reduce the highest ambient RH to 40%.

The supply of silica gel is typically large enough for unattended continuous operation for at least one week, under conditions of high ambient humidity. A larger supply can be used to minimize frequency of replacement. As the silica gel becomes saturated with water, the pump will have to increase the flow to achieve the target RH, for the same ambient RH. Thus, there is a known relation between the degree of saturation, the pump flow, and the ambient RH. Consequently, because the both the actual ambient RH and the pump flow rate are continuously monitored, it is possible to have remote off-site access to determine when the silica gel requires change.

EXAMPLE 5

Single Channel Continuous Ambient Mass Monitor

Another aspect of the invention is a single channel method and device for the continuous ambient particulate mass monitoring. This system has only one path (channel) through which the sample gas flows and has two particulate matter collectors, e.g., Nucleopore® filters arranged in series. Preferably, these represent different segments of a single membrane filter tape. The pressure drop across a first Nucleopore® filter is used to determine ambient particle mass concentration, and the pressure drop across a second Nucleopore® filter is used to correct the pressure drop for the first filter due to changes in flow, temperature, and humidity. The advantage of the single channel compared to the dual channel system is that it is less expensive, although it is not as sensitive. However, for circumstances where maximum sensitivity is not required, the single channel configuration may be more appropriate than a dual channel configuration.

A schematic diagram of a single channel particulate monitoring device is shown in FIG. 4. One pressure transducer (range of about 25 inches of water) (1) measures the total pressure drop across an initial Nucleopore® filter (2), which measures the mass concentration of particles in the sample air. The other pressure transducer (3) measures the total pressure drop across a second Nucleopore® filter (4). Since the air passing through the second Nucleopore® filter has at least 99% of its particles removed by the high efficiency HEPA filter (5), changes in pressure drop across the second Nucleopore filter correspond only to changes in temperature, humidity, and flow rate. Consequently, the difference between the signals from the first and second transducers corresponds to the change in particle mass concentration. Pump (6) draws sample air through the system.

EXAMPLE 6

Measurement of Mass Concentration of Ambient Particles as a Function of Particle Size This apparatus and method simultaneously measures the size distribution and mass concentration of particles below 10 $\mu$m (PM$_{10}$). Air samples are first drawn through a system of conventional and virtual impactors, separating the particles into channels with the following size ranges: $\leq$0.15 $\mu$m,; $\leq$0.3 $\mu$m,; $\leq$0.6 $\mu$m,; $\leq$1 $\mu$m,; $\leq$2.5 $\mu$m,; 2.5–5.0 $\mu$m,; and 2.5–10.0 $\mu$m, aerodynamic diameter. Gas comprising the separate size particles of each channel are each passed through a diffusion dryer that reduces the relative humidity of the air sample to 40%, thereby removing particle-bound water. The particle-containing gas from each channel is passed through a separate particulate matter collector, e.g., a Nucleopore® membrane filter tape (first position on a membrane filter tape) and the pressure across the tape is measured. Downstream of the first particulate matter collector is a HEPA filter followed by a second particulate matter collector (second position on the same membrane filter tape), to allow correction for the combined effects of temperature, humidity, and flow rate. The pressure drop across each particulate matter collector, e.g., filter tape, per unit time, is directly proportional to the mass concentration of the sample air. Thus, the system allows for continuous determination of the mass concentration for each of the seven size ranges of the particulate matter.

An apparatus for measurement of the mass concentration of ambient particles as a function of particle size is shown in FIG. 5. Air samples are first drawn through a conventional PM$_{10}$ impactor (1) at 4 liters/min to remove particles larger than 10 $\mu$m. Subsequently the sampled aerosol is drawn through a virtual impactor (2) with a 50% cutpoint at 2.5 $\mu$m. The minor flow of the virtual impactor (0.25 liters/min) contains all the particles $\geq$2.5 $\mu$m, concentrated by a factor of 4/0.25, along with the original ambient concentration of PM$_{2.5}$ particles (size $\leq$2.5 $\mu$m). The major flow (3.75 liters/min) contains only PM$_{2.5}$ particles. The minor flow is then split in two equal flows (0.125 liters/min). One flow (channel 1) (3) is drawn directly through a particle mass measuring unit (see below) to determine particle mass for size 2.5–10 $\mu$m. The other flow (channel 2)(4) is drawn through a 5.0 $\mu$m cutpoint conventional impactor, prior to passing through a mass measuring unit, to determine particle mass for size 2.5–5.0 $\mu$m.

The major flow (3.75 liters/min) of the virtual impactor is split in five equal flows, for channels 3–7 (0.75 liters/min each). The flow in channel 3 (5) determines the total PM$_{2.5}$ concentration (size $\leq$2.5 $\mu$m). The flows in channels 4–7 (6–9) are drawn through separate conventional impactors that act as preselective inlets, successively removing particles larger than their respective impactor/inlet cutpoints: 1.0; 0.6; 0.3; and 0.15 $\mu$m aerodynamic diameter.

The particles in each channel are drawn through mass measuring units. Typically, each measuring unit contains a diffusion dryer, a particulate matter collector (e.g., Nucleopore® filter), a filter transport and sealing system, a pressure transducer, and a vacuum pump. Downstream of the first particulate matter collector is a HEPA filter followed by a second particulate matter collector, and a second pressure transducer, to allow correction for the combined effects of temperature, humidity, and flow change (rate). Each channel determines the mass concentration of particles in its respective size range: 1) 2.5–10.0 $\mu$m ("coarse mass"); 2) 2.5–5.0 $\mu$m; 3) $\leq$2.5 $\mu$m (PM$_{2.5}$); 4) $\leq$1 $\mu$m (PM$_1$); 5) $\leq$0.6 $\mu$m (PM$_{0.6}$); 6) $\leq$0.3 $\mu$m (PM$_{0.3}$); and 7) $\leq$0.15 $\mu$m (PM$_{0.15}$) PM$_{10}$ is determined by summing the concentrations for coarse mass, 2.5–10.0 $\mu$m (determined from channel 1) and "fine mass" (PM$_{2.5}$, from channel 3). The sampled particles are dried after and not before the impactors so that particles entering the units are classified at ambient humidity, but the mass measurements correspond to particle mass with the contribution to mass from particle-bound water removed. This is in accordance to the U.S. EPA reference method for PM$_{10}$, which requires filter equilibration of sample filters at a relative humidity of 40% or less prior to gravimetric determination of particle mass concentration. If particles were dried prior to the size separation by impaction, the measured size distribution would be different from the ambient size distribution, due to shrinkage of water-containing particles.

The mass measuring units of each channel can be connected to a data acquisition system that digitizes the voltage outputs of the pressure transducers for each channel and transforms those data into values for the particle mass concentration. A detailed description of the individual components of the system and the procedures for their characterization is presented below.

10 μm Cutpoint Conventional Impactor

The Harvard-Marple $PM_{10}$ conventional impactor removes particles larger than 10 μm from the air sample. The performance of the impactor at 4 liters/min has been extensively characterized (Marple, V. A., Rubow, K. L., Turner, W., and Spengler, J. D., *JAPCA* 37:1303–1307, 1987).

2.5 μm Cutpoint Virtual Impactor

After the $PM_{10}$ conventional impactor (c.i.), particles pass through a 4 liter/min 2.5 μm cutpoint virtual impactor (v.i.). Both the v.i. and the c.i. use the principle of inertia to separate particles by size. Both accelerate particles through a round nozzle. For the v.i., a collection probe replaces the impaction surface of the c.i., and a fraction of the flow (0.25 liter/min) passes straight through, containing all the particles with size above the cutpoint ("minor flow"). The minor flow thus increases the concentration of the larger particles by a factor of 4/0.25, but it also contains the original concentration of smaller particles. The major flow (3.75 liter/min) contains only particles below the cutpoint (2.5 μm).

The design of the virtual impactor is based on the Stokes number equation which relates the cutpoint to the impactor's design and operating parameters. The Stokes number is given by the following formula (Hinds, W. C., Aerosol Technology, John Wiley & Sons Inc., New York, 1982):

$$St = \frac{\rho_p U d_p^2 C_c}{9 \mu W} = \frac{4 \rho_p d_p^2 C_c Q}{9 \pi \mu W^3} \quad (1)$$

where $d_p$ is the 50% cutpoint size, W is the acceleration nozzle diameter, U is the average velocity of the jet, Q is the sampling flow rate, $\rho_p$ is the particle density, $\mu$ is the dynamic viscosity of the air, and $C_c$ is the Cunningham slip correction factor. Typically, for a round jet virtual impactor, a St value of about 0.4 corresponds to the 50% cutpoint (Marple, V. A. and Chien, C. M., *Environ. Sci. & Technol.* 8:976–985, 1980; Sioutas, C., Koutrakis, P, and Wolfson, J. M., *Aerosol Sci. & Technol.* 21 (2):137–149, 1994a). The acceleration nozzle diameter will be 0.2 cm and the collection nozzle diameter will be 0.3 cm. The ratio of the diameters of the two nozzles is chosen to be 1.5 in order to minimize particle losses (Sioutas, C., Koutrakis, P., and Olson, B. A., *Aerosol Sci. & Technol.* 21:223–235, 1994b). The actual particle collection efficiency and losses can be determined as a function of particle size using monodisperse fluorescent aerosols (size range 1.0–4.0 μm), using the method of Sioutas et al. 1994b, supra. Aqueous suspensions of fluorescent microspheres ($\rho$=1.047 g/cm$^3$; Fluoresbrite, Polysciences, Warrington, Pa.) can be nebulized. The nebulized aerosol passes through a 1-liter chamber with ten Polonium 210 ionizing units (Staticmaster, NRD Inc.) to reduce the particle charge distribution to close to the Boltzmann equilibrium. After the neutralizer, the aerosol is mixed with room air in a 3-liter chamber and passes through the virtual impactor, with a glass fiber filters on both the major and minor flows, to trap the fluorescent particles.

At the end of each test, the glass fiber filters and the inside surfaces of the impactor are extracted with ethyl acetate to dissolve the latex particles and release their fluorescent dye into solution. The quantities of the fluorescent dye in the extraction solutions are measured using a fluorescence spectrophotometer (FD-300 Fluorescence Detector, GTI, Concord, Mass.). The collection efficiency of the impactor for a certain particle size can be determined by dividing the amount of fluorescence in the minor flow by the sum of the fluorescence of the major and minor flows. Particle losses can be determined by dividing the amount of fluorescence on the internal surfaces of the impactor by the sum of fluorescence on major flow, minor flow, and internal surfaces.

Design and Evaluation of the Conventional Impactors

The purpose of the impactor/inlet is to remove particles larger than a certain size. For channels 4–7, particles will be drawn at 0.75 liters/min through an inlet and accelerated in a round nozzle. The flow rate in channel 2 is 0.125 liters/min. A porous metal plate, wet with mineral oil, is used as the impaction substrate to minimize particle bounce (a problem frequently encountered in impactors, Rao, A. K., and Whitby, K. T., *J. Aerosol Sci.* 9:87, 1978), for each of the conventional impactors. Similarly to the virtual impactor design, the dimensions of the different impactor nozzles is based on the Stokes number equation. The design and operating parameters of the five impactor/inlets are shown in Table 4. The cutpoints have been based on St=0.25.

TABLE 4

Design and operating parameters of the five impactors/inlets.

| Channel No. | Nozzle Diameter (cm) | Cutpoint Aerodynamic Diameter (μm) |
|---|---|---|
| 2 | 0.12 | 5.0 |
| 4 | 0.078 | 1.0 |
| 5 | 0.058 | 0.6 |
| 6 | 0.040 | 0.3 |
| 7 | 0.030 | 0.15 |

The actual particle collection efficiency and losses are determined as a function of particle size using monodisperse fluorescent aerosols (0.05–10.0 μm), as described above. The only difference is that the test system consists of the impactor followed by a 4.7 cm glass fiber filter. At the end of each run, the impactor's plate and the glass fiber filter are extracted with ethyl acetate. The collection efficiency of the impactor for a certain particle size is determined by dividing the amount of fluorescence on the plate by the sum of the amounts on the plate and the downstream filter. Particle losses are determined by extracting the inside surfaces of the impactor and comparing the fluorescence of the extracts to the sum of the fluorescence on the collection plate, the downstream filter, and the inside surfaces.

Design and Evaluation of the Diffusion Dryers

Diffusion dryers reduce relative humidity (RH) of the air sample to no more than 40%, removing water from the hygroscopic particles, which increase in size with increasing ambient RH (Tang I. N., Munkelwitz, H. R., and Davies, J. G., *J. Aerosol Sci.* 9:505–511, 1978; Koutrakis, P., Wolfson, J. M., Spengler, J. D., Stern, B., and Franklin, C. A., *J. Geophys. Res.* 94:6442–6448, 1989). Ambient particles contain very little water at these RH levels (Tang, I. N., *J. Aerosol Sci.* 7:361–371 1976).

The diffusion dryer uses a tube made of a semi-permeable membrane, such as a Nafion® membrane, which allows only water vapor to pass through. The ambient air sample passes through the membrane tube, while dry air is passed on the outside of the tube. The efficiency of transfer is very high, so only a short length of tubing is required (less than 5 cm, for a sample flow of 0.15 liters/min). The relative humidity of the sample air is measured downstream from the pressure drop measuring system, and a feedback system will continuously control the flow of dry air, allowing the system to maintain sample air at 40±5% RH, when ambient RH is 40% or higher, and to shut off the flow of dry air, when ambient RH is below 40%. Particle penetration through the dryer is measured by generating polydisperse aerosols in an atomizer and measuring their concentration upstream and downstream of the dryer with the TSI Scanning Mobility Particle Sampler (SMPS Model 3934, TSI Inc., St. Paul, Minn.) for $0.05<d_p<0.7$ μm, and the Aerodynamic Particle Sizer (APS) (Model 3310, TSI Inc., St. Paul. Minn.) for $d_p>0.7$ μm.

Design of the Mass Measuring Units

Impaction becomes more important with increase in particle size, so filter face velocities lower than 12 cm/sec (used for fine particles) are needed for larger particles to achieve a linear change in pressure drop per unit mass concentration per unit time. Thus for each channel the optimum pore size and optimum effective face velocity are separately determined, as previously described, to maximize sensitivity. Typically, a filter transport system exposes a new segment of the filter membrane every 30 min to minimize adsorption/desorption phenomena.

Data Reduction

Mass concentration values are calculated for each of the seven channels in the system, based on the empirically determined slope of concentration vs pressure drop for each size range. The total coarse particle concentration, $C_{2.5 \leqq d \leqq 10}$, is the value for channel 1 ($C'_{2.5 \leqq d \leqq 10}$) corrected by the amount of fine particles, $PM_{2.5}$ (from channel 3, see below). Since the coarse particles for channel 1 (contained in the minor flow) have increased in concentration above ambient by a factor of 4/0.25, while the fine particle concentration in the minor flow is the same as ambient, the corrected value, $C_{2.5 \leqq d \leqq 10}$, is calculated as follows:

$$C_{2.5 \leqq d \leqq 10} = (02.5/4)(C'_{2.5 \leqq d \leqq 10} - (0.25/4)(PM_{2.5}))$$

The fraction of coarse mass below 5 μm, $C_{2.5 \leqq d \leqq 5}$ is the value for channel 2, $C'_{2.5 \leqq d \leqq 5}$, also corrected by the amount of fine particles:

$$C_{2.5 \leqq d \leqq 5} = (0.25/4)(C'_{2.5 \leqq d \leqq 5} - (0.25/4)(PM_{2.5}))$$

The difference, $C_{2.5 \leqq d \leqq 10}$, is $C_{5 \geqq d \geqq 10}$, the fraction between 5 and 10 μm. The total fine mass concentration (size below 2.5 μm), $PM_{2.5}$, is determined by channel 3, since the major flow of the virtual impactor has the fine particles at ambient concentration, with all the coarse particles removed. Channels 4–7 determine $PM_1$, $PM_{0.6}$, $PM_{0.3}$, and $PM_{0.15}$, respectively. The difference between the concentrations for channels 4 and 3 is the value for particles between 2.5 and 1 μm, $C_{1 \leqq d \leqq 2.5}$. Successive differences are used to calculate the concentrations for the remaining sizes, $C_{0.6 \leqq d \leqq 1}$, $C_{0.3 \leqq d \leqq 0.6}$, and $C_{0.3 \leqq d \leqq 0.15}$. For channel 7, $PM_{0.15}$, is the concentration for all particles with size below 0.15 μm. The concentration for all particles below 10 μm, $PM_{10}$, is calculated as the sum of the coarse particles, $C_{2.5 \leqq d \leqq 10}$, and the fine particles, $PM_{2.5}$.

Tests are conducted to determine the optimum Nucleopore® filter pore size and effective face velocity for each channel. The method has a limit of detection of 5 μg/m$^3$ per hour, for a pore size of 2 μm. A higher sensitivity, however, can be required when classifying $PM_{10}$ in as many as seven size channels. A smaller pore size, D, is used to increase the rate of pressure drop increase per unit mass collected, since the pressure drop is proportional to $1/D^3$. The pore size will be larger than the upper particle size for a given channel (i.e., the impactor/inlet cutpoint) in order to avoid particle collection by sieving. Therefore, for each channel, the increase in the pressure drop across the filter per unit time and unit mass concentration ($\Delta P/(C_m \cdot t)$) is determined for different values of D, starting from the cutpoint of the impactor/inlet of the specific channel. The target sensitivity for channels 1–7 is 0.5 μg/m$^3$ per hour.

The system can provide accurate measurements because losses or gains of semi-volatiles are negligible for short sample durations with low filter face velocity.

EXAMPLE 7

Determination of Particle Density and Particle-Bound Water

This system allows for the determination of the particle mass, density and mean diameter of both ambient and dry aerosols. The apparatus and method also allows for the determination of the particle-bound water, as well as molalities, water activity, water activity coefficients, and other bulk aqueous parameters. This method makes it possible to obtain information regarding the physico-chemical properties of hygroscopic aerosols which cannot be obtained with existing methods.

An apparatus useful for the determination of particle density and particle-bound water is depicted in FIG. 6. The apparatus has a 10 μm cutpoint conventional impactor for removing particles larger than 10 μm from a gas sample (1). Downstream of the 10 μm cutpoint conventional impactor is a 2.5 μm cutpoint virtual impactor for dividing the gas sample into a component comprising fine mass (less than or equal to 2.5 μm) and a component comprising coarse mass (2.5–10 μm) (2). For each size range of particles (fine and coarse) there are two channels, one with and one without diffusion dryers (3A & 3B), so as to allow for the measurement dried and undried particles; fine mass undried (channel 1), fine mass dried (channel 2), coarse mass undried (channel 3), coarse mass dried (channel 4). Each channel has a set of three particulate matter collectors, e.g. Nucleopore® filter stages, arranged in series (4A–C; 5A–C; 6A–C; 7A–C), a HEPA filter located downstream from the three particulate matter collectors (4D, 5D, 6D, 7D), a fourth particulate matter collector positioned downstream from the HEPA filter used as a control for temperature, humidity and flow variations (4E, 5E, 6E, 7E). The four particulate matter collectors are part of a separate automatic filter changing mechanism, with four sections of the tape used simultaneously, which correspond to the filters 4A, B, C, and E; 5A, B, C, and E; 6A, B, C, and E; and 7A, B, C, and E. Four pressure transducers (4F–I, 5F–I, 6F–I, 7F–I) for measuring the pressure drop across the each set of four particulate matter collectors (4F–I, 5F–I, 6F–I, 7F–I). Each channel has a pump (4J, 5J, 6J, 7J) to draw the air sample through the series of filters. Measurement of the pressure drop across each filter allows for the determination of particle mass concentration, average density, and mean diameter. The difference in mass between the dried and undried aerosols is a quantitative measurement of particle-bound water. A computer and equations described below can be used to convert the raw data on the pressure drop across the filters into values for particle mass concentration, average density, mean diameter, and particle-bound water.

The described apparatus utilizes a single channel design for each of the four paths (3, 4, 5, and 6). It is possible to obtain higher sensitivity for this method by using a two channel design for each of the four paths as used in the Continuous Ambient Mass Monitor (CAMM), supra, 1995.

The apparatus and accompanying method allow for the accurate, sensitive, relatively inexpensive and easy measurement of particle mass, density, mean diameter and bound water. Measurement of these particle parameters can be very useful in understanding the behavior of hygroscopic aerosols, since these data can be used to determine important thermodynamic parameters such as molarity, water activity, activity coefficients, molar volumes, and other bulk aqueous properties. Therefore, this apparatus and method address several important issues and make a significant contribution to the field of ambient air particle measurements.

The pressure drop is measured simultaneously across each of the three filters during particle collection. The apparatus includes a filter transport system which exposes and replaces simultaneously three different filter tapes. An explanation is given below which describes how simultaneous measurements of the pressure drop across the three particulate matter collectors are used to determine the average particle density.

In the present invention which has three filters (a, b, and c) in series, it is necessary to make calculations using polydisperse particle size distributions, to take into account the changes in particle size distribution as the air sample passes through each of the three filters. The particle collection efficiency ($\eta$) is calculated as follows (Smith, T. N. and Phillips, C. R., *Environ. Sci. & Technol.* 9:564–568, 1975):

$$\eta = 1.1 \rho_p^{0.5} d_p/D \quad (1)$$

where $\rho_p$ is the particle density, $d_p$ is the particle diameter, and D is the membrane pore diameter. Equation (1) is used to determine the collection efficiency, due to interception of particles on the edges of the filter pores, for the first two filters a and b:

and $$\eta_a = 1.1 \rho_p^{0.5} D_a/D = c_{mb}/c_{ma} \quad (2)$$

$$\eta_b = 1.1 \rho_p^{0.5} D_b/D = c_{mc}/c_{mb} \quad (3)$$

where $D_a$ and $D_b$ are the particle mass mean diameters upstream and downstream the first filter, a; D is the filter pore size (which is the same for all three filters); $\rho_p$ is the average density; and $c_{ma}$, $c_{mb}$ and $c_{mc}$ are the particle mass concentrations upstream the filters a, b, and c, respectively.

Equations (2) and (3) assume that the average particle density for each of the fine and coarse particle fractions is independent of particle size. This is a reasonable assumption especially for the fine mode where particles are to a great extent internally mixed (Koutrakis, P. and Kelly, B., *J. Geophys. Res.* 98:7141–7147, 1993). The implication of this assumption is that the particle size distribution changes, which occur as the air sample passes through the battery of the three filters, are due virtually exclusively to the size differences among the different particles. This is because passage through each successive filter increases the relative fraction of smaller size particles compared to the fraction of larger particles, due to higher efficiency of collection for larger particles. In fact, this is effectively true because the relative variation of $\rho^{0.5}$ in each of the fine and coarse modes is at least one order of magnitude less than that of individual particle size ranges, which extends from 0.05 to 2.5 $\mu$m, for the fine mode, and extends from 2.5 to 10 $\mu$m, for the coarse mode. Based on equations (2) and (3), and using published theoretical and experimental results (Spurny, K., Lodge, J. P., Frank, E. R., Sheesley, D. C., *Environ. Sci. & Technol.* 3:453–464. 1969; Smith, T. N. and Phillips, C. R., *Environ. Sci. & Technol.* 9:564–568, 1975; Hinds, W. C. (1982) *Aerosol Technology*, John Wiley & Sons Inc., New York; John, W., Reischl, G., Goren, S., Plotkin, D. *Atmos. Environ.* 12:1555–1557, 1978) it is possible to determine the collection efficiencies for filters a and b, $\eta_a$ and $\eta_b$ respectively, as a function of the pressure drop across each of the three filters $\Delta P_a$, $\Delta P_b$, $\Delta P_c$, respectively:

$$\eta_a = 1.1 \rho_p^{0.5} D_a/D = (D^2-(K_2/\Delta P_b)^{0.66})/(D^2-(K_2/\Delta P_a)^{0.66}) \quad (4)$$

$$\eta_b = 1.1 \rho_p^{0.5} D_b/D = (D^2-(K_2/\Delta P_c)^{0.66})/(K_2-(K_2/\Delta P_b)^{0.66}) \quad (5)$$

where $K_2$ is a constant which depends on the face velocity, particle density, filter pore diameter, and filter porosity, and $\Delta_a$, $\Delta_b$, and $\Delta_c$ are the pressure drops across filters a, b, c, respectively.

The particle mean diameter $D_a$ is equal to:

$$D_a = f_1 d_{p1} + f_2 d_{p2} + \ldots f_n d_{pn} \quad (6)$$

where $f_i$ is the fraction of particle mass that has a diameter $d_{pi}$. The mean particle diameter downstream the filter, $D_b$, can be expressed as a function of $D_a$:

$$°_b = f_1 d_{p1} - 1.1\rho_p^{0.5} d_{p1}/D + f_2 d_{p2} - 1.1\rho_p^{0.5} d_{p2}/D + \ldots f_n d_{pn} 1.1 \rho_p^{0.5} d_{pn}/D$$

$$10 = (f_1 d_{p1} + f_2 d_{p2} + \ldots f_n d_{pn})(1 - 1.1\rho_p^{0.5}/D) = D_a(1 - 1.1\rho_p^{0.5}/D) \quad (7)$$

By combining equations (4), (5) and (7) we can express the particle density, $\rho_p$, as a function of the filter pore diameter and the pressure drop across the three identical filters a, b and c:

$$\varrho_p = 0.82 D^2 \left[ 1 - \frac{(D^2 - (K_2/\Delta P_a)^{0.66})(D^2 - (K_2/\Delta P_a)^{0.66})}{(D^2 - (K_2/\Delta P_b)^{0.66})^2} \right]^2 \quad (8)$$

Subsequently, equation (4) can be used to determine the mean particle diameter $D_a$ as a function of particle density, filter pore diameter, and the pressure drop across filters a and b:

$$D_a = 0.9 \rho_p^{-0.5} D (D^2 - (K_2/\Delta P_b)^{0.66})/(D^2 - (K_2/\Delta P_a)^{0.66}) \quad (9)$$

The mass and size of particles already collected on any filter medium can vary with subsequent changes in ambient relative humidity during sampling. Therefore, when the system is used without reducing sample air relative humidity to remove particle-bound water, it is expected that the pressure drop measurement across the filter will change when relative humidity changes take place during the sampling period. For multi-hour samples where relatively large quantities of particles have accumulated on the filter (on the order of 50 to 500 $\mu$g), pressure drop increases due to the uptake or loss of water by the previously accumulated particles can be more important than those associated with the incremental particle collection. Therefore, it is not possible to measure particle-bound water using such long sampling periods. To overcome this problem the apparatus of the present invention exposes each segment of the Nucleopore® membrane for only about thirty minutes. Typically, there are negligible changes in ambient relative humidity over these short durations. However, since the method includes continuous measurement of RH, it allows rejecting of data for sampling periods during which RH changes exceed a preselected threshold.

Measurement of particle-bound water mass and mean particle size

Below is a summary of model calculations for the measurement of particle-bound water mass and mean particle size. These are based on the use of sulphate particles which can be generated with different values of known strong acidity content and size under different humidity conditions at 25° C. These particles can be generated by nebulizing aqueous solutions of $(NH_4)_2SO_4/H_2O_4$ mixtures (Koutrakis et al., *J. Geophys. Res.* 94:6642–6648, 1989; and Koutrakis and Kelly, *J. Geophys. Res.* 98:7141–7147, 1993).

First, the relationship between water activity, $\alpha_w$, and solution molality, m, is determined using fifth-order polynomial expressions:

$$\alpha_w = \Sigma b_i m^i \quad (10)$$

where i=1 . . . 5 and $\alpha_w$=% RH/100. The $b_i$ coefficients have been measured for the different sulfate salts (ammonium sulfate, letovicite and ammonium bisulfate, Tang, I. N. *Atmos. Environ.* 14:814–828, 1980). Therefore, it is possible to determine $\alpha_w$, for different molalities from zero up to a value that corresponds to a water activity equal to the eutonic (deliquescence) point, $\alpha_w$, of the corresponding salt. After establishing the relationship between water activity and molality, the particle molality is determined by measuring the relative humidity. Molality is defined as the amount of solute moles per mass of solvent. Thus the total particle-bound water is determined by dividing the total amount of sulfate moles collected using the micro-orifice impactor (Marple, V. A., Rubow, K. L., and Behm, S. M., *Aerosol Sci. & Technol.* 14:434–446, 1991) by the calculated molality of the sulfate solute. As has been previously demonstrated, the water and solute molar volumes, $v_w$ and $v_s$, can be expressed as functions of the solution ionic strength, I, which is determined using the calculated molality, m (Koutrakis and Kelly, 1993 supra). Subsequently, the solution (or particle) density is obtained using the following equation:

$$\rho_p = \rho_0 + c(M_s - \rho_0 v_s) \quad (11)$$

where $M_s$ is the molecular weight of the solvent, $\rho_o$ is the density of the water and c is the solution concentration, which is determined as follows:

$$c = 1/(v_s + v_w/M_{wm}) \quad (12)$$

$$D_a = \rho^{-0.5} D_{ae} \quad (13)$$

Finally, the mean particle diameter is determined using the mean particle aerodynamic diameter, $D_{ae}$, measured by the micro-orifice impactor.

As shown above, it is possible to independently determine the different parameters such as water mass, density, size, and particle mass for the generated hygroscopic aerosols.

Other embodiments are within the following claims.

What is claimed is:

1. Apparatus for the continuous ambient mass monitoring of $PM_{10}$ in a gas sample, comprising:

a conventional inertial impactor able to remove particles greater than 10 μm in diameter in gaseous communication with said sample gas, a virtual impactor downstream of said conventional inertial impactor and in gaseous communication with said gas after passage of said gas through said inertial impactor and able to separate said gas into a first component comprising particles less than 2.5 μm in diameter and a second component comprising particles between 2.5 μm in diameter and 10 μm in diameter, a first diffusion dryer positioned downstream of said virtual impactor through which passes said first gas component and able to reduce the relative humidity in said first gas component to 40% or lower, a second diffusion dryer positioned downstream of said virtual impactor through which passes said second gas component and able to reduce the relative humidity in said second gas component to 40% or lower, a first particulate matter collector positioned downstream of said first diffusion drier through which passes said first gas component, a second particulate matter collector positioned downstream of said second diffusion drier through which passes said second gas component, a first HEPA filtered positioned downstream of said first particulate matter collector through which passes said first gas component, a second HEPA filtered positioned downstream of said second particulate matter collector through which passes said second gas component, a third particulate matter collector positioned downstream of said first HEPA filter through which passes said first gas component, a fourth particulate matter collector positioned downstream of said second HEPA filter through which passes said second gas component, a first, second, third, and fourth pressure transducer to measure differential pressure across said first, second, third, and fourth particulate matter collectors, a first pump to cause said first gas component to pass through said first and said third particulate matter collectors, and a second pump to cause said second gas component to pass through said second and said fourth particulate matter collectors.

2. Method for the continuous mass monitoring of $PM_{10}$ in a gas sample, comprising the steps of:

providing an apparatus comprising a conventional inertial impactor able to remove particles greater than 10 μm in diameter in gaseous communication with said gas, a virtual impactor downstream of said conventional inertial impactor and in gaseous communication with said gas after passage of said gas through said inertial impactor and able to separate said gas into a first component comprising particles less than 2.5 μm in diameter and a second component comprising particles between 2.5 μm in diameter and 10 μm in diameter, a first diffusion dryer positioned downstream of said virtual impactor through which passes said first gas component and able to reduce the relative humidity in said first gas component to 40% or lower, a second diffusion dryer positioned downstream of said virtual impactor through which passes said second gas component and able to reduce the relative humidity in said second gas component to 40% or lower, a first particulate matter collector positioned downstream of said first diffusion drier through which passes said first gas component, a second particulate matter collector positioned downstream of said second diffusion drier through which passes said second gas component, a first HEPA filter positioned downstream of said first particulate matter collector through which passes said first gas component, a second HEPA filter positioned downstream of said second particulate matter collector through which passes said second gas component, a third particulate matter collector positioned downstream of said first HEPA filter through which passes said first gas component, a fourth particulate matter collector positioned downstream of said second HEPA filter through which passes said second gas component, a first, second, third, and fourth pressure transducer to measure differential pressure across said first, second, third, and fourth particulate matter collectors, a first pump to cause said first gas component to pass through said first and said third particulate matter collectors, a second pump to cause said second gas component to pass through said second and said fourth particulate matter collectors, causing said gas to pass to said first, second, third, and fourth particulate matter collectors, and measuring the pressure differential between said first and third particulate matter collectors and said second and fourth particular matter collectors as a basis for determining the amount of $PM_{10}$ in said gas sample.

3. Apparatus for measuring the mass concentration of ambient particles in a gas sample as a function of the particle size, comprising:

a conventional impactor with a 10 $\mu$m cutpoint, a virtual impactor with a 2.5 $\mu$m cutpoint positioned downstream from said conventional impactor so as to separate said gas sample into a first gas component comprising particles with a size range of aerodynamic diameter of $\leq 2.5$ $\mu$m and into a second gas component comprising particles with a size range between 2.5 and 10 $\mu$m, a first channel positioned downstream of said virtual impactor containing a conventional impactor with a size cutoff of 0.15 $\mu$m so that upon passage of a first portion of said first gas component through said conventional impactor, particles that remain in said channel comprise a size range of aerodynamic diameter of $\leq 0.15$ $\mu$m, a second channel positioned downstream of said virtual impactor containing a conventional impactor with a size cutoff of 0.3 $\mu$m so that upon passage of a second portion of said first gas component through said conventional impactor, particles that remain in said channel comprise a size range of aerodynamic diameter of $\leq 0.3$ $\mu$m, a third channel positioned downstream of said virtual impactor containing a conventional impactor with a size cutoff of 0.6 $\mu$m so that upon passage of a third portion of said first gas component through said conventional impactor, particles that remain in said channel comprise a size range of aerodynamic diameter of $\leq 0.6$ $\mu$m, a fourth channel positioned downstream of said virtual impactor containing a conventional impactor with a cutoff of 1.0 $\mu$m so that upon passage of a fourth portion of said first gas component through said conventional impactor, particles that remain in said channel comprise a size range of aerodynamic diameter of $\leq 1$ $\mu$m, a fifth channel positioned downstream of said virtual impactor so that upon passage of a fifth portion of said first gas component through said channel particles that remain in said channel comprise a size range of aerodynamic diameter of $\leq 2.5$ $\mu$m, a sixth channel positioned downstream of said virtual impactor containing a conventional impactor with a cutoff of 5.0 $\mu$m so that upon passage of a first portion of said second gas component through said conventional impactor, particles that remain in said channel comprise a size range of aerodynamic diameter of 2.5 to 5.0 $\mu$m, a seventh channel positioned downstream of said virtual impactor so that so that upon passage of a second portion of said second gas component through said channel, particles that remain in said channel comprise a size range of aerodynamic diameter of 2.5 to 10.0 $\mu$m, a diffusion dryer for each channel positioned downstream of said impactor in each said channel, a first particulate matter collector positioned downstream of said diffusion dryer for each channel, a HEPA filter positioned downstream of said particulate matter collector for each channel, a second particulate matter collector positioned downstream of said HEPA filter for each channel, and a first and second pressure transducer for each channel for measuring the pressure drop per unit time across said first and second particulate matter collector in each channel, and a pump for each channel to cause said portion of said first or second component of said gas sample to flow through said first and second particulate matter collector for each said channel.

4. Method for measuring the mass concentration of ambient particles in a gas sample as a function of the particle size, comprising the steps of:

providing an apparatus comprising a conventional impactor with a 10 $\mu$m cutpoint, a virtual impactor with a 2.5 $\mu$m cutpoint positioned downstream from said conventional impactor so as to separate said gas sample into a first gas component comprising particles with a size range of aerodynamic diameter of $\leq 2.5$ $\mu$m and into a second gas component comprising particles with a size range between 2.5 and 10 $\mu$m, a first channel positioned downstream of said virtual impactor containing a conventional impactor with a size cutoff of 0.15 $\mu$m so that upon passage of a first portion of said first gas component through said conventional impactor, particles that remain in said channel comprise a size range of aerodynamic diameter of $\leq 0.15$ $\mu$m, a second channel positioned downstream of said virtual impactor containing a conventional impactor with a size cutoff of 0.3 $\mu$m so that upon passage of a second portion of said first gas component through said conventional impactor, particles that remain in said channel comprise a size range of aerodynamic diameter of $\leq 0.3$ $\mu$m, a third channel positioned downstream of said virtual impactor containing a conventional impactor with a size cutoff of 0.6 $\mu$m so that upon passage of a third portion of said first gas component through said conventional impactor, particles that remain in said channel comprise a size range of aerodynamic diameter of $\leq 0.6$ $\mu$m, a fourth channel positioned downstream of said virtual impactor containing a conventional impactor with a cutoff of 1.0 μm so that upon passage of a fourth portion of said first gas component through said conventional impactor, particles that remain in said channel comprise a size range of aerodynamic diameter of $\leq 1$ μm, a fifth channel positioned downstream of said virtual impactor so that upon passage of a fifth portion of said first gas component through said channel, particles that remain in said channel comprise a size range of aerodynamic diameter of $\leq 2.5$ μm, a sixth channel positioned downstream of said virtual impactor containing a conventional impactor with a cutoff of 5.0 μm so that upon passage of a first portion of said second gas component through said conventional impactor, particles that remain in said channel comprise a size range of aerodynamic diameter of 2.5 to 5.0 μm, a seventh channel positioned downstream of said virtual impactor so that so that upon passage of a second portion of said second gas component through said channel, particles that remain in said channel comprise a size range of aerodynamic diameter of 2.5 to 10.0 μm, a diffusion dryer for each channel positioned downstream of said impactor in each said channel, a first particulate matter collector positioned downstream of said diffusion dryer for each channel, a HEPA filter positioned downstream of said particulate matter collector for each channel, a second particulate matter collector positioned downstream of said HEPA for each channel, a first and second pressure transducer for each channel for measuring the pressure drop per unit time across said first and second particulate matter collector in each channel, a pump for each said channel which causes said gas to pass through said first and said second particulate matter collector in said channel, causing said portions of said first and said second gas components to pass to said first and said second particulate matter collector of said channels, and measuring the pressure differential between said first and second particulate matter collector for each channel as a basis for determining the mass concentration of ambient particles in said gas sample as a function of particle size.

5. Apparatus for measuring particle-bound water and particle density in ambient particles in a gas sample, comprising a 10 μm cutpoint conventional impactor for removing particles larger than 10 μm from said gas sample, a virtual impactor with a 2.5 μm cutpoint positioned downstream from said conventional impactor so as to separate said gas sample into a first gas component comprising particles with a size range of aerodynamic diameter of $\leq 2.5$ μm and into a second gas component comprising particles with a size range between 2.5 and 10 μm, a first channel positioned downstream of said virtual impactor for passage of a first portion of said first gas component and a second channel with a diffusion drier positioned downstream of said virtual impactor for passage of a second portion of said first gas component, a third channel positioned downstream of said virtual impactor for passage of a first portion of said second gas component and a fourth channel with a diffusion drier positioned downstream of said virtual impactor for passage of a second portion of said second gas component, a set of three particulate matter collectors arranged in series and positioned downstream of said diffusion drier in said second and said fourth channels and positioned downstream of said virtual impactor in said first and third channels, a HEPA filter positioned downstream of the three particulate matter collectors in each said channel, a fourth particulate matter collector positioned downstream of said HEPA filter in each said channel, a first, second, third, and fourth pressure transducer for measuring the pressure drop across each said particulate matter collectors for each said channel, and a pump positioned downstream of said fourth particulate matter collector for each said channel to cause said first or second portion of said first or second component to pass to said first, second, third, and fourth particulate matter collectors for each said channel.

6. Method for measuring particle-bound water and particle density in ambient particles contained in a gas sample, comprising the steps of:

providing an apparatus comprising a 10 μm cutpoint conventional impactor for removing particles larger than 10 μm from said gas sample, a virtual impactor with a 2.5 μm cutpoint positioned downstream from said conventional impactor so as to separate said gas sample into a first gas component comprising particles with a size range of aerodynamic diameter of $\leq 2.5$ μm and into a second gas component comprising particles with a size range between 2.5 and 10 μm, a first channel positioned downstream of said virtual impactor for passage of a first portion of said first gas component and a second channel with a diffusion drier positioned downstream of said virtual impactor for passage of a second portion of said first gas component, a third channel positioned downstream of said virtual impactor for passage of a first portion of said second gas component and a fourth channel with a diffusion drier positioned downstream of said virtual impactor for passage of a second portion of said second gas component, a set of three particulate matter collectors arranged in series and positioned downstream of said diffusion drier in said second and fourth channels and positioned downstream of said virtual impactor in said first and third channels, a HEPA filter positioned downstream of said three particulate matter collectors in each said channel, a fourth particulate matter collector positioned downstream of said HEPA filter in each said channel, a first, second, third, and fourth pressure transducer for measuring the pressure drop across each said particulate matter collectors for each said channel, a pump positioned downstream of each said fourth particulate matter collector for each said channel to cause said first or said second portion of said first or second gas component to pass to said first, second, third, and fourth particulate matter collectors for each said channel, and causing said first and said second portion of said first and second gas component to pass to said first, second, third, and fourth particulate matter collector in said channels, and measuring the pressure differential between said first, second, third, and fourth particulate matter collectors in each channel as a basis for determining the particle-bound water and particle density in ambient particles contained in said gas sample.

* * * * *